United States Patent
Wang et al.

(10) Patent No.: US 10,350,308 B2
(45) Date of Patent: Jul. 16, 2019

(54) MOLECULAR PROBES FOR IMAGING MYELIN

(75) Inventors: Yanming Wang, Cleveland, OH (US); Changning Wang, Melrose, MA (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 873 days.

(21) Appl. No.: 13/806,795

(22) PCT Filed: Jun. 30, 2011

(86) PCT No.: PCT/US2011/042618
§ 371 (c)(1),
(2), (4) Date: Apr. 3, 2013

(87) PCT Pub. No.: WO2012/003334
PCT Pub. Date: Jan. 5, 2012

(65) Prior Publication Data
US 2013/0209357 A1 Aug. 15, 2013

Related U.S. Application Data

(60) Provisional application No. 61/359,865, filed on Jun. 30, 2010.

(51) Int. Cl.
| | |
|---|---|
| A61K 51/00 | (2006.01) |
| A61M 36/14 | (2006.01) |
| A61K 49/00 | (2006.01) |
| A61K 51/04 | (2006.01) |
| C07D 277/66 | (2006.01) |

(52) U.S. Cl.
CPC ...... *A61K 49/0021* (2013.01); *A61K 49/0032* (2013.01); *A61K 51/0453* (2013.01); *C07D 277/66* (2013.01); *A61K 49/0017* (2013.01)

(58) Field of Classification Search
None
See application file for complete search history.

(56) References Cited

U.S. PATENT DOCUMENTS

| | | | | |
|---|---|---|---|---|
| 4,762,701 A * | 8/1988 | Horan et al. | | 424/1.17 |
| 6,534,041 B1 * | 3/2003 | Licha et al. | | 424/9.6 |
| 2002/0142244 A1 * | 10/2002 | Takashima et al. | | 430/138 |
| 2006/0073541 A1 * | 4/2006 | Kilgore | | 435/40.5 |

OTHER PUBLICATIONS

Wang, H., et al., "Coherent anti-stocks Raman scattering imaging of axonal myelin in live spinal tissue", Biophysical Journal, Jul. 1, 2005, vol. 89, pp. 581-591.
McCamant, D. et al., "Femosecond broadband stimulated Raman: A new approach for high-performance vibrational sepctroscopy", Applied Spectroscopy, Nov. 30, 2003, vol. 57 1317-1323.
Wang, Y, et al., "In Vivo Quantification of myelin changes in the vertebrate nervous system", The Journal of Neuroscience, Nov. 18, 2009, vol. 29, pp. 14663-14669.
Roy, R., et al., "Fluorescence-enhanced three dimensional lifetime imaging: a phantom study", Physics in Medicine and Biology, Jul. 15, 2007, vol. 52, pp. 4155-4170.
Gioux, S. et al., "Low-frequency wide-field fluorescence imaging using a high-power near-infrared light . . . ", Journal of Biomedical Optics, Mar. 30, 2010, vol. 15, p. 0265005 1-5.

* cited by examiner

*Primary Examiner* — Michael G. Hartley
*Assistant Examiner* — Melissa J Perreira
(74) *Attorney, Agent, or Firm* — Tarolli, Sundheim, Covell & Tummino LLP

(57) ABSTRACT

A molecular probe for use in the detection of myelin in a subject includes a compound having the general formula selected from the group consisting of: formula (I), and pharmaceutically acceptable salts thereof.

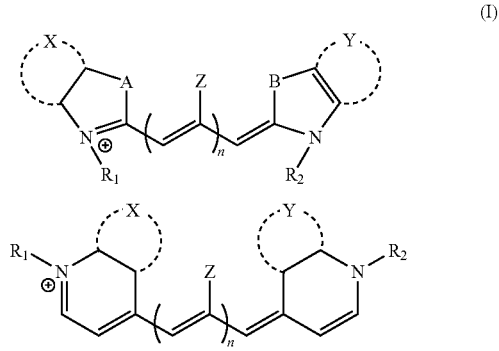

22 Claims, 13 Drawing Sheets

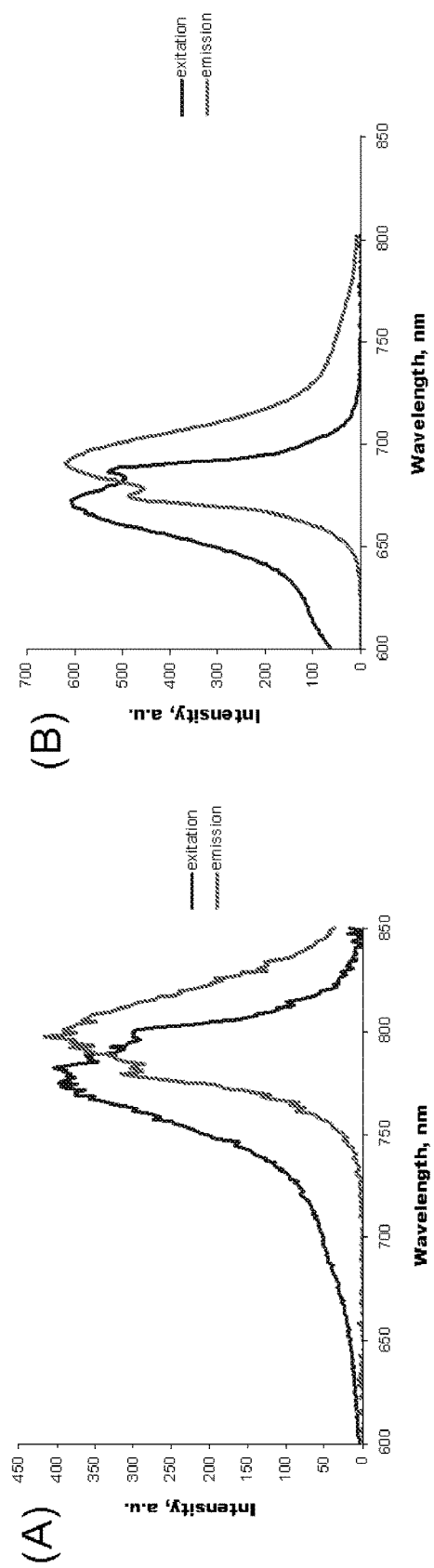
Figs. 1A-B

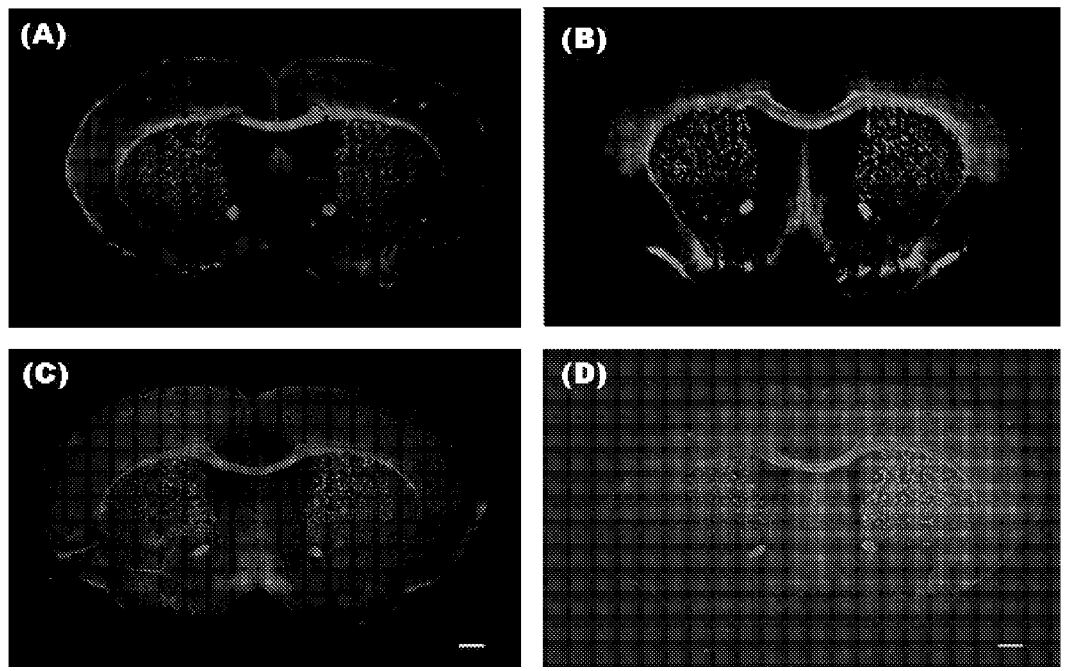
Figs. 2A-D
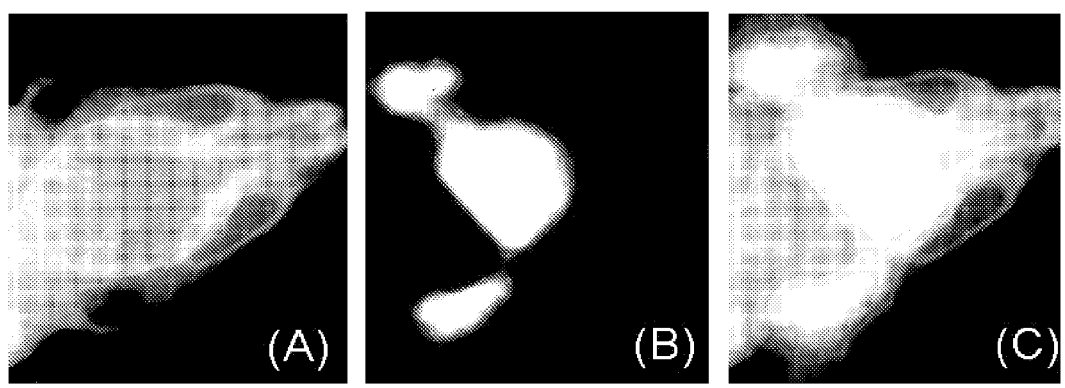
Figs. 3A-C

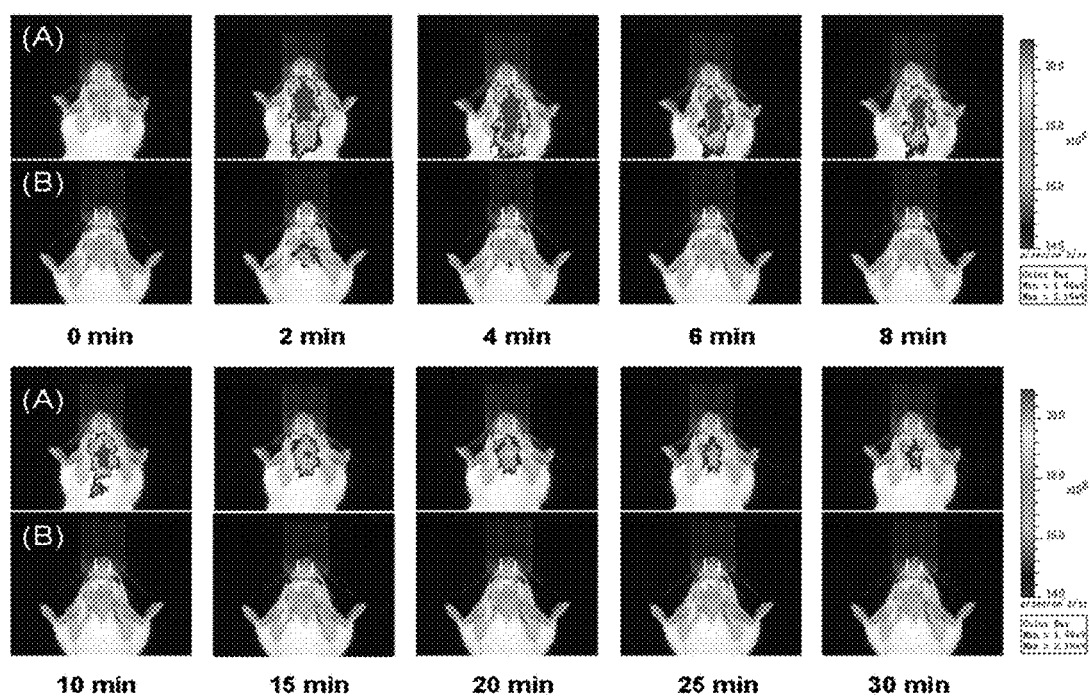
Figs. 4A-B

Figs. 6A-B

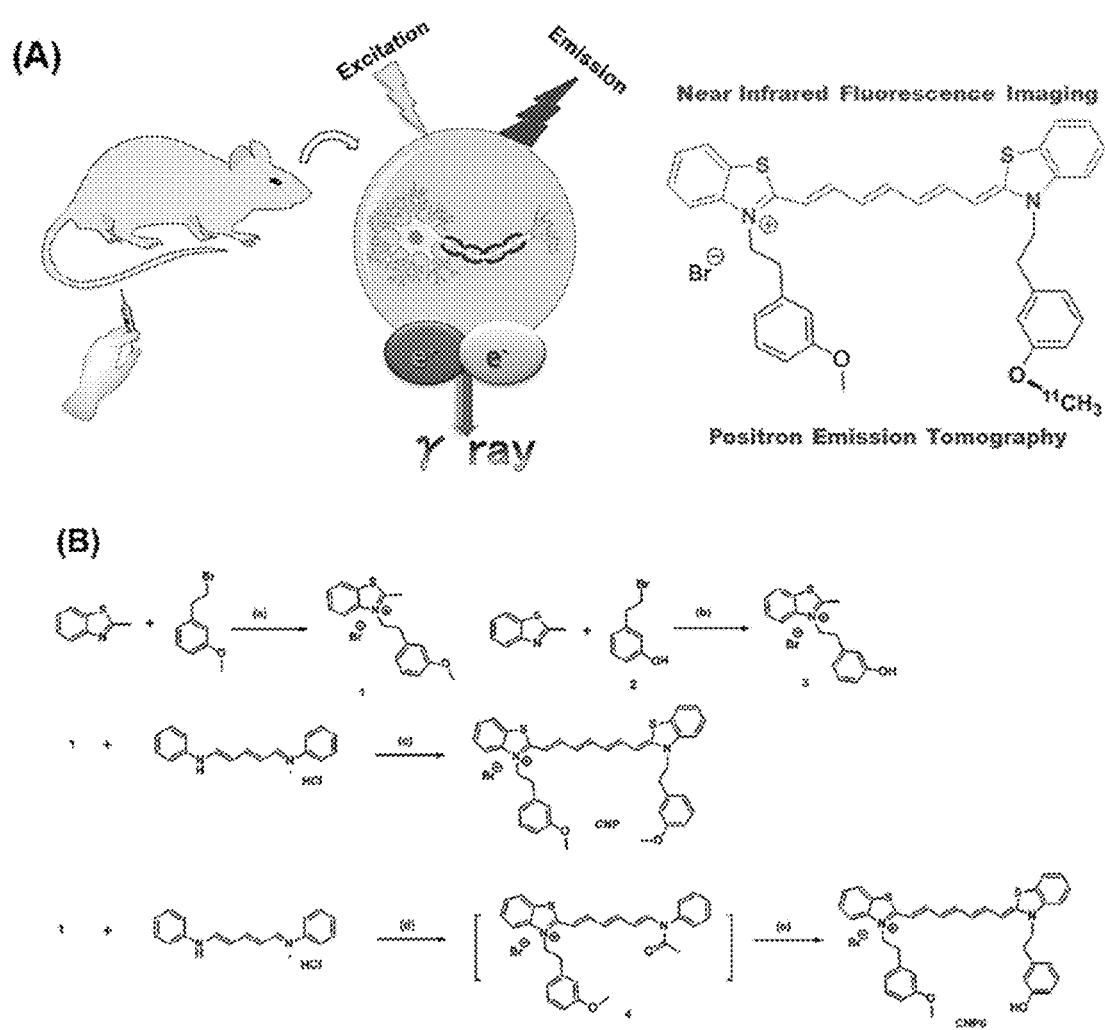
Figs. 8A-B

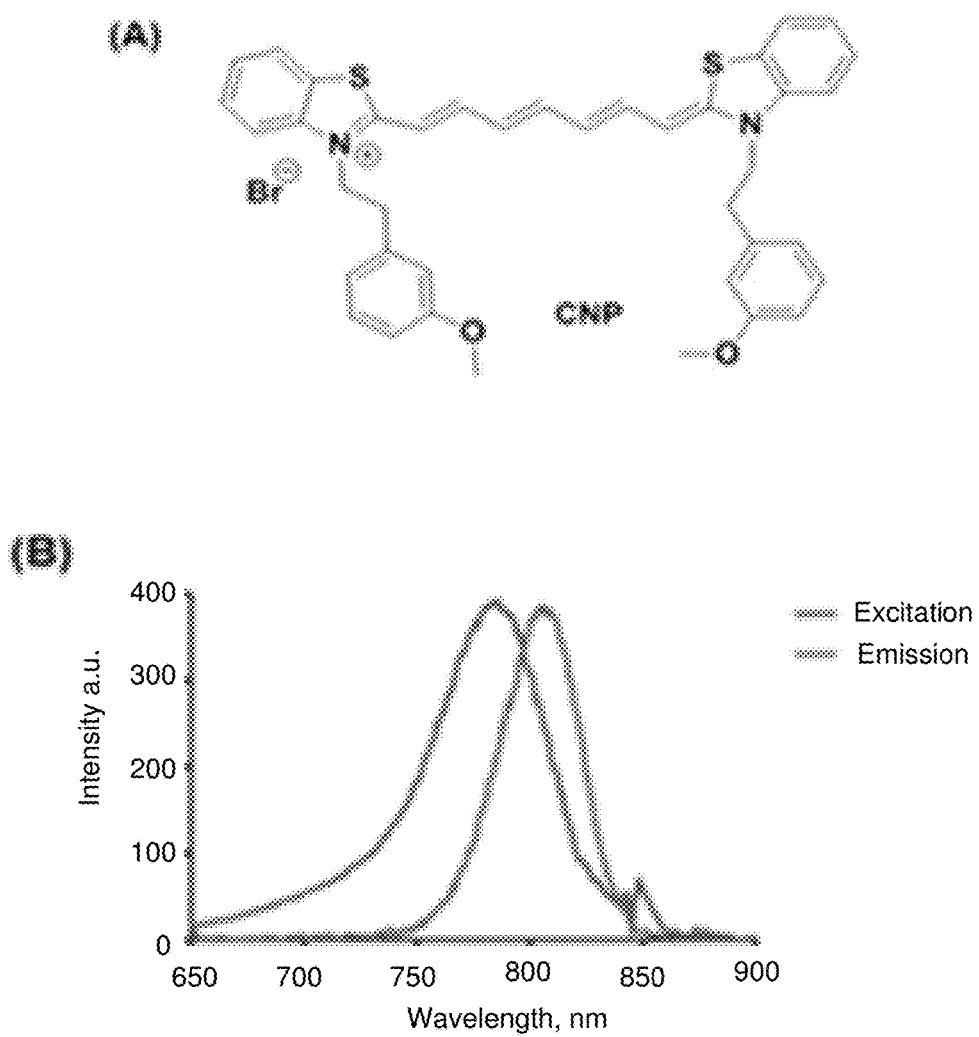
Figs. 9A-B

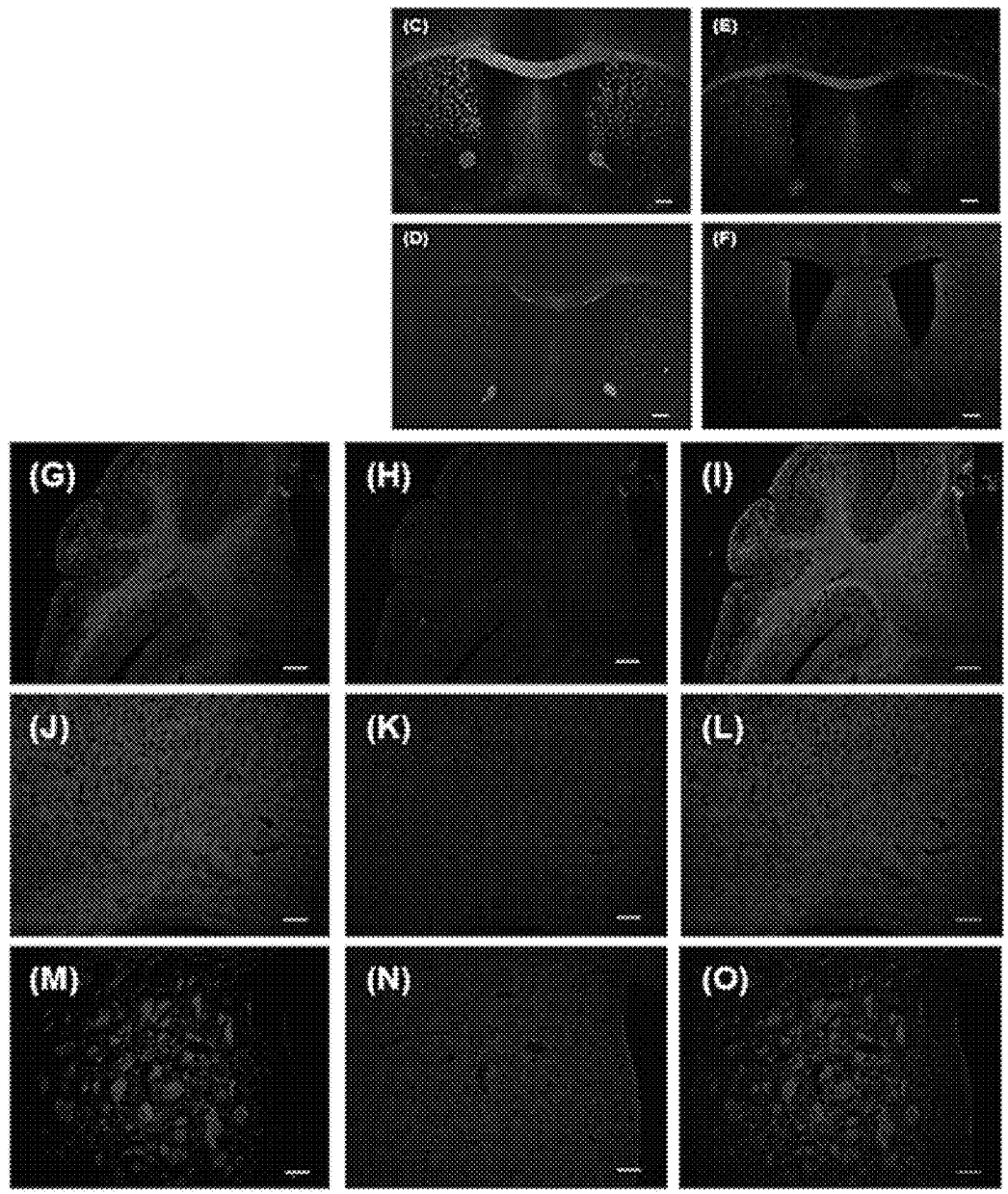
Figs. 9C-O

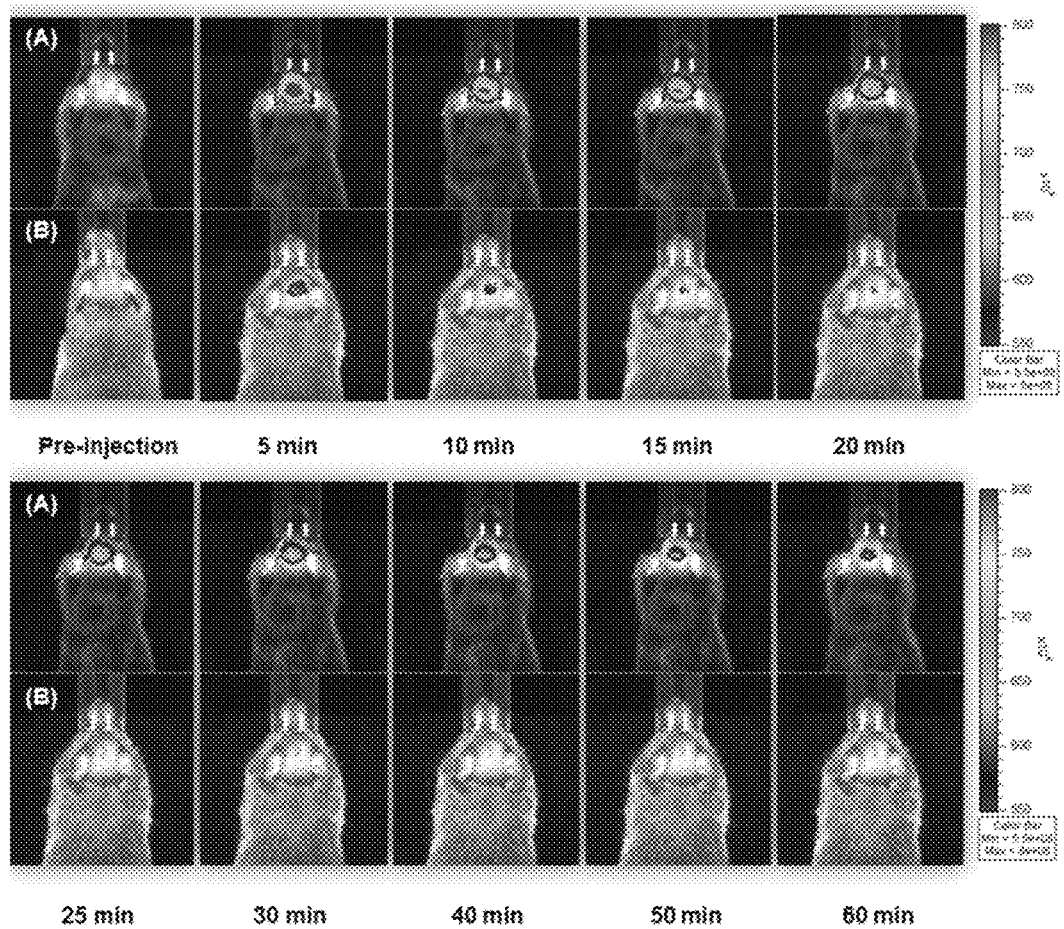
Figs. 10A-B

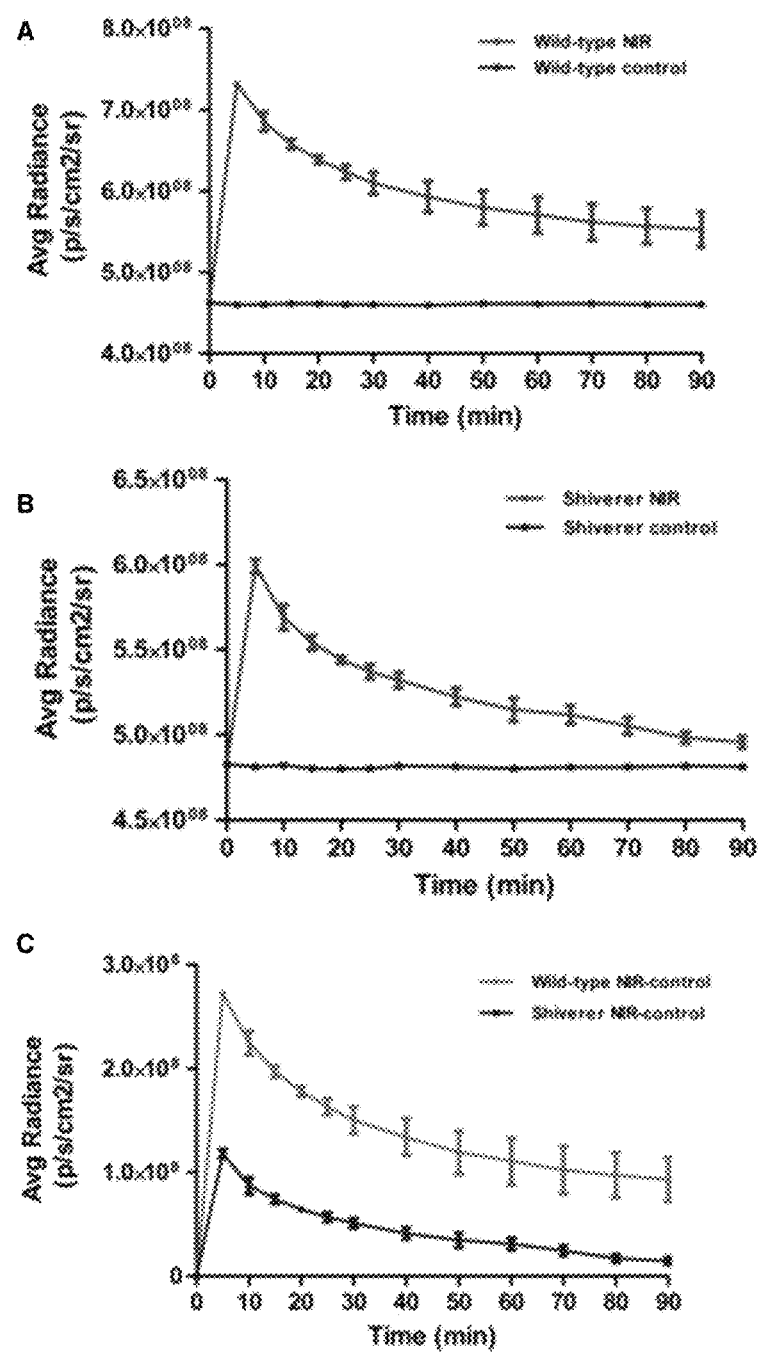
Figs. 11A-C

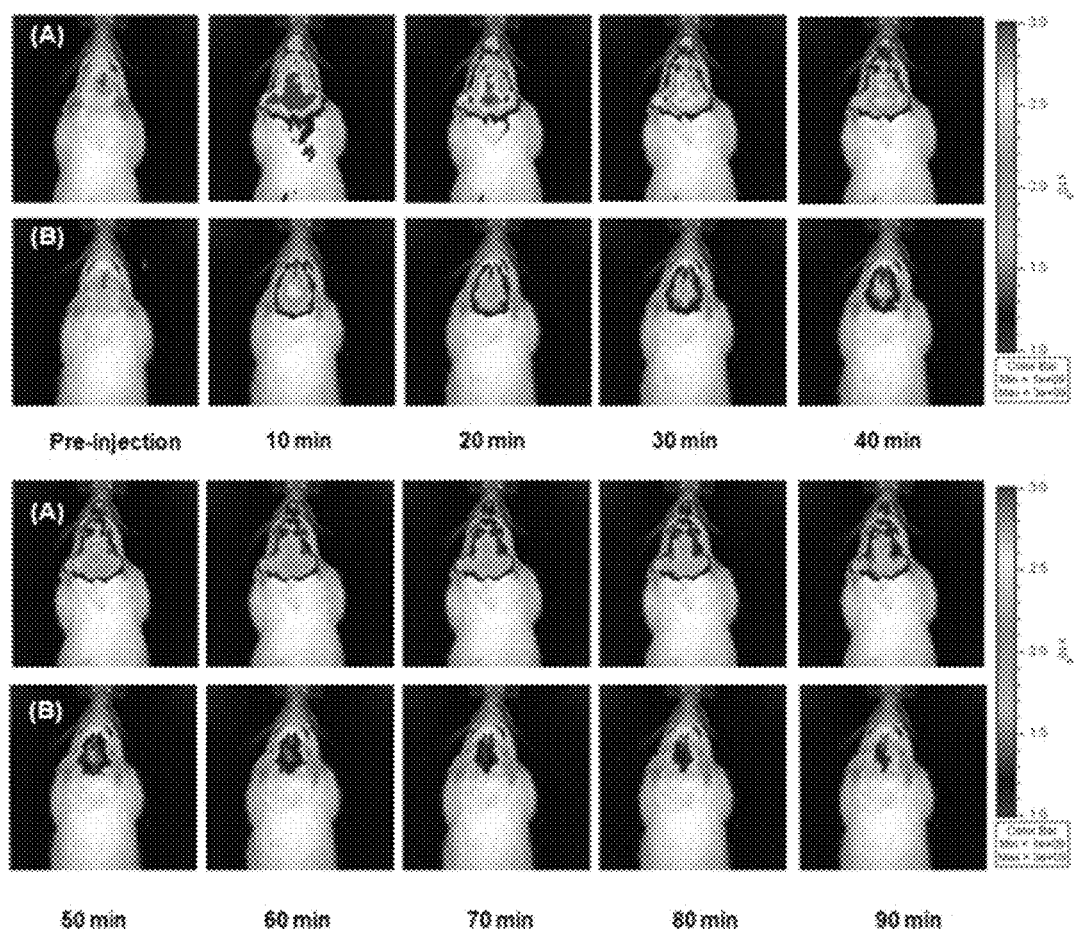
Fig. 12A-B

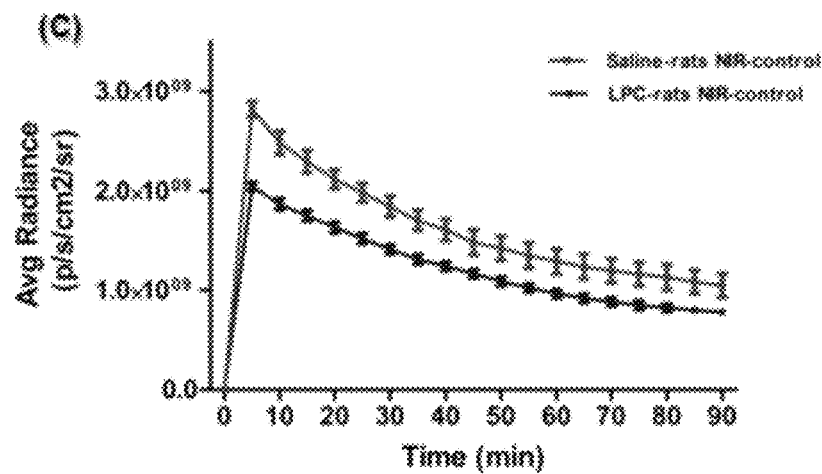
Fig. 12C
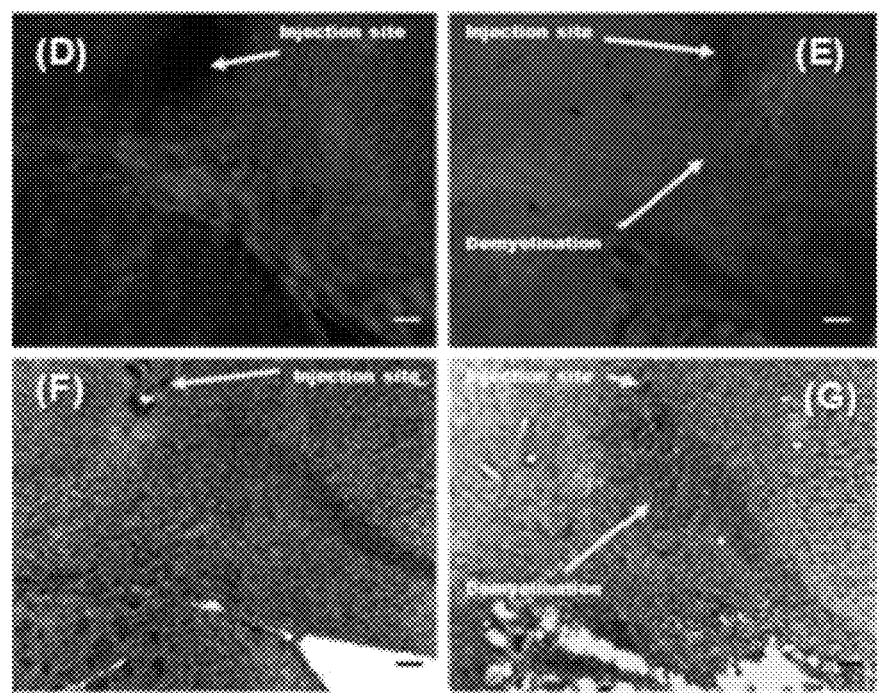
Fig. 12D-G

MOLECULAR PROBES FOR IMAGING MYELIN

RELATED APPLICATION

This application is a National Phase Filing of PCT/US2011/042618, filed Jan. 30, 2011, which claims priority from U.S. Provisional Application No. 61/359,865, filed Jun. 30, 2010, the subject matter of which are incorporated herein by reference in their entirety.

GOVERNMENT FUNDING

This invention was made with government support under Grant No. R01 NS061837, awarded by The National Institutes of Health. The United States government may have certain rights to the invention.

TECHNICAL FIELD

This application relates to molecular probes and to methods of their use, and particularly relates to molecular probes that can selectively bind to and/or label myelinated regions of the nervous system.

BACKGROUND OF THE INVENTION

Molecular imaging has entered a new era in which different imaging modalities have become available for in vivo studies of disease-defining targets. These imaging modalities include positron emission tomography (PET), single photon emission computed tomography (SPECT), magnetic resonance imaging (MRI), and optical imaging, which complement each other in many ways. For example, PET provides high sensitivity but relatively low resolution while MRI provides high resolution but low sensitivity. PET provides high quantitative capacity compared to SPECT but production of PET radiotracers is limited, as it requires a cyclotron to produce positron-emitting carbon-11 and fluorine-18. Production of SPECT radiotracers is more affordable as it uses generators that are more readily available. PET, SPECT, and MRI are the primary imaging modalities in clinical settings.

One of the key targets for molecular imaging is myelin membranes. In the vertebrate nervous systems, myelination is one of the most fundamental biological processes that provide a unique structure that fosters rapid and efficient conduction of impulses along axons. Destruction or changes in myelination have been considered as a causative event in numerous neurological diseases such as multiple sclerosis (MS). Significant efforts have been made to delineate molecular mechanism of demyelination/remyelination and develop novel therapeutics aimed at myelin repair. However, there is still a need to directly detect and quantify myelin changes in vivo in both preclinical and clinical settings.

Magnetic resonance imaging (MRI) is widely used in brain imaging in MS and other myelin-related diseases. However, MRI is not a specific measure of myelination, as MR signals reflects only a change in tissue water content, which is a non-specific measure of the overall changes in macroscopic tissue injury.

Near-infrared (NIR) fluorescence imaging is a powerful tool for in vivo preclinical studies of disease progression in animal models. Use of NIR imaging depends on the availability of target-specific molecular probes, for example, those that can be delivered through membranes or the intact blood-brain barrier. In general, light absorption decreases with increasing wavelength. Below 650 nm, tissue absorption leads to small penetration in a depth of only a few millimeters. The absorption coefficient of tissue is considerably smaller in the near infrared region (650 nm-900 nm) and light can penetrate more deeply into the tissues to depths of several centimeters.

Recently, near-infrared fluorescence imaging, have been explored for in vivo detection of amyloid-βdeposits using a near-infrared dye developed by Gremlich et al. (Gremlich, H. U. et al. In vivo detection of amyloid-βdeposit by near-infrared imaging using an oxazine-derivative probe. *Nat. Biotechnology.* 23, 577-583 (2005)). In order to make the detection and quantification of myelin more practical and less burdensome, novel near-infrared imaging probes are needed to take advantage of the optical imaging modality, such as bioluminescence imaging and fluorescent molecular tomography that have recently been developed.

SUMMARY

This application relates to molecular probes for use in the detection of myelin in a subject. The molecular probes include a compound having a general formula selected from the group consisting of:

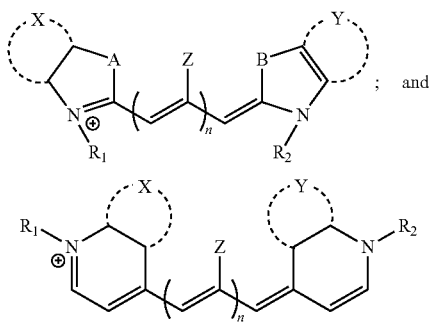

wherein n is an integer from 1 to 10; A, B each independently represent $CR'_2$, O, S, NH, $CH_2CH_2$, CH=CH; $R_1$, $R_2$, R', and Z each independently represent H, alkyl, alkenyl, alkynyl, and/or an aryl group; X and Y each independently represent

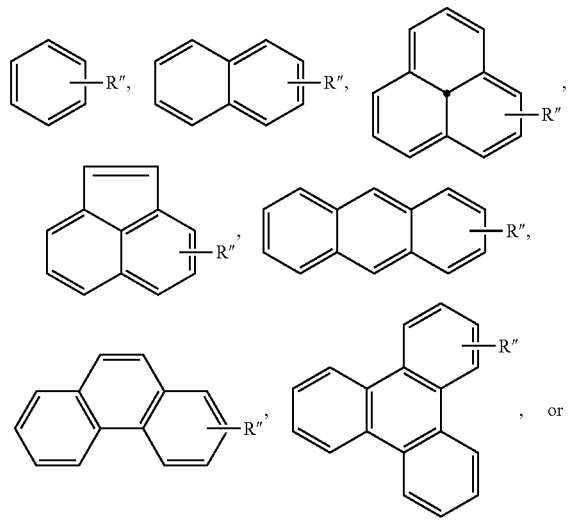

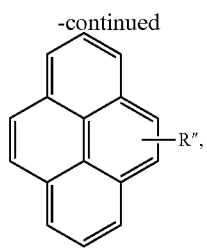

wherein R"=H, alkyl, alkenyl, alkynyl or an aryl group; and pharmaceutically acceptable salts thereof.

In some aspects of the application, $R_1=R_2$. In some aspects, A=B. In some aspects X=Y. In other aspects, n is an integer from 3 to 10.

In some aspects, the molecular probe can include an additional imaging moiety that allows the molecular probe to be detected by more than one imaging modality. In some embodiments the imaging moiety can include a radiolabel that is conjugated to the molecular probe. The radiolabel can be selected from the group consisting of C-11, F-18, I-124, I-123, I-131, and Tc-99m. In some aspects, the imaging moiety that is conjugated to the molecular probe can include a magnetic resonance contrast agent allows the molecular probe to be viewed by magnetic resonance imaging. The magnetic resonance contrast agent can include, for example, a chelating agent, gadolinium, or F-19 that is bound to the molecular probe to facilitate or enhance magnetic resonance imaging.

In certain aspects of the application, the molecular probe includes a compound having the formula:

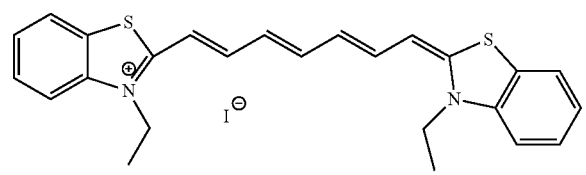 [SMILES: CCN1\C(=C/C=C/C=C/C=C/c2sc3ccccc3[n+]2CC)Sc2ccccc21 ; [I-]]

and pharmaceutically acceptable salts thereof.

In certain aspects, the molecular probe includes a compound having the formula:

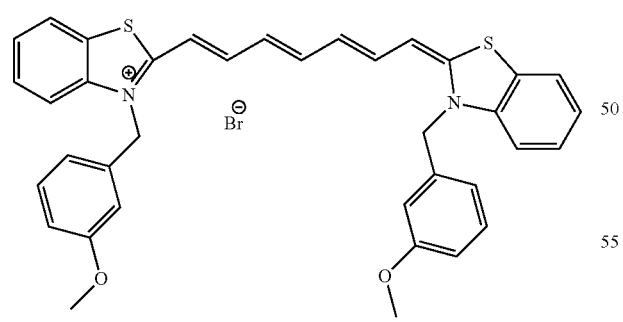

and pharmaceutically acceptable salts thereof.

The application also relates to a method of detecting myelin in a subject's tissue. The myelin can be associated with nerves of the central system and/or the peripheral system. The tissue can include brain tissue, spinal tissue, and other tissue associated with the peripheral nervous system. In some aspects, the tissue can be myelinated tissue at a surgical site.

The method includes administering to the subject a near-infrared probe that includes a compound having a general formula selected from the group consisting of:

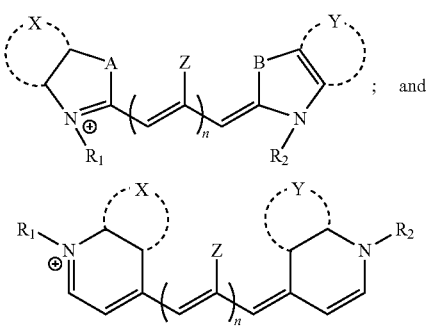
; and wherein n is an integer from 1 to 10; A, B each independently represent $CR'_2$, O, S, NH, $CH_2CH_2$, CH=CH; $R_1$, $R_2$, R', and Z each independently represent H, alkyl, alkenyl, alkynyl and/or an aryl group; X and Y each independently represent

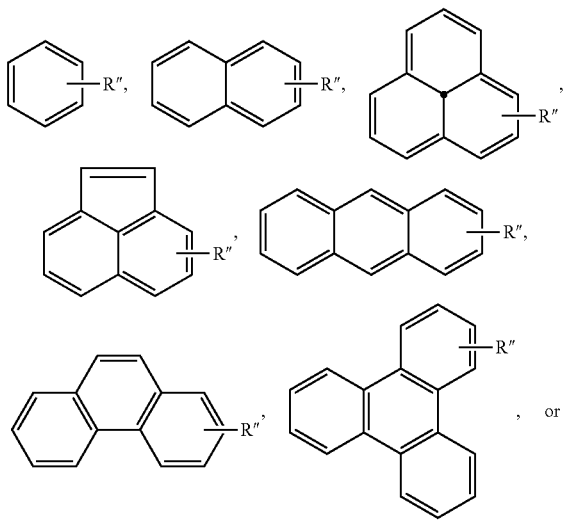

wherein R"=H, alkyl, alkenyl, alkynyl or an aryl group; and pharmaceutically acceptable salts thereof. Following, administration of the molecular probe, the subject's tissue, e.g., brain, can be visualized using an imaging modality to determine the location, distribution, and/or amount of the molecular probe that is bound to and/or labels the myelin.

In some aspects of the application, $R_1=R_2$. In other aspects, n is an integer from 3 to 10. In other aspects, A=B. In some aspects X=Y.

In some aspects, the molecular probe can include an additional imaging moiety that allows the molecular probe to be detected by more than one imaging modality. In some embodiments the imaging moiety can include a radiolabel that is conjugated to the molecular probe. The radiolabel can be selected from the group consisting of C-11, F-18, I-124, I-123, I-131, and Tc-99m. In some aspects, the imaging moiety that is conjugated to the molecular probe can include a magnetic resonance contrast agent allows the molecular probe to be viewed by magnetic resonance imaging. The magnetic resonance contrast agent can include, for example, a chelating agent, gadolinium, or F-19 that is bound to the molecular probe to facilitate or enhance magnetic resonance imaging.

In certain aspects, the molecular probe includes a compound having the formula:

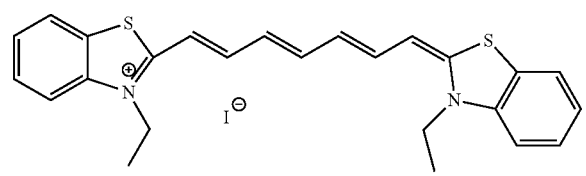 [SMILES: CCN1\C(=C/C=C/C=C/C=C/c2sc3ccccc3[n+]2CC)Sc2ccccc21 ; [I-]]

and pharmaceutically acceptable salts thereof.

In certain aspects, the molecular probe includes a compound having the formula:

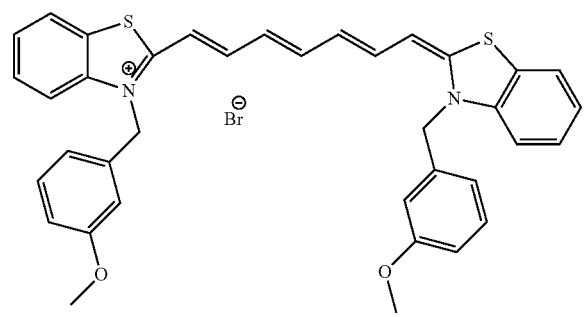 [SMILES: COc1cccc(CN2\C(=C/C=C/C=C/C=C/c3sc4ccccc4[n+]3Cc3cccc(OC)c3)Sc3ccccc32)c1 ; [Br-]]

and pharmaceutically acceptable salts thereof.

In some aspects, the imaging modality can include a near-infrared fluorescence imaging modality. In some aspects, the imaging modality can include a fluorescence tomography imaging modality. The molecular probe can be administered parenterally to the subject. In some aspects, the subject can be a mammal, such as a human.

The application also relates to a method of detecting a myelination related disorder in a subject. The method includes administering to the subject a molecular probe that includes a compound having the general formula selected from the group consisting of:

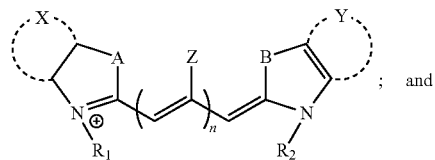 ; and

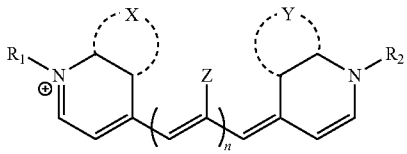

wherein n is an integer from 1 to 10; A, B each independently represent $CR'_2$, O, S, NH, $CH_2CH_2$, CH=CH; $R_1$, $R_2$, R', and Z each independently represent H, alkyl, alkenyl, alkynyl and/or an aryl group; X and Y each independently represent

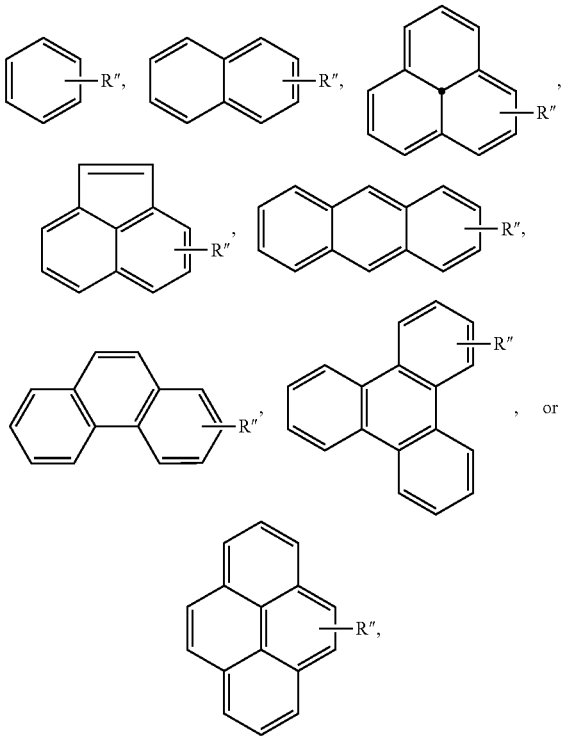

wherein R''=H, alkyl, alkenyl, alkynyl or an aryl group; and pharmaceutically acceptable salts thereof. The distribution and/or amount of the molecular probe bound to and/or labeling myelin in the subject's neural tissue is then detected, measured, and/or quantified and compared to a control. A decreased distribution and/or amount of the molecular probe compared to the control is indicative of a decrease in myelination of the neural tissue.

In some aspects of the application, $R_1$=$R_2$. In some aspects, A=B. In some aspects, X=Y. In other aspects, n is an integer from 3 to 10.

In some aspects, the molecular probe can include an additional imaging moiety that allows the molecular probe to be detected by more than one imaging modality. In some embodiments the imaging moiety can include a radiolabel that is conjugated to the molecular probe. The radiolabel can be selected from the group consisting of C-11, F-18, I-124, I-123, I-131, and Tc-99m. In some aspects, the imaging moiety that is conjugated to the molecular probe can include a magnetic resonance contrast agent allows the molecular probe to be viewed by magnetic resonance imaging. The magnetic resonance contrast agent can include, for example, a chelating agent, gadolinium, or F-19 that is bound to the molecular probe to facilitate or enhance magnetic resonance imaging.

In certain aspects, the molecular probe includes a compound having the formula:

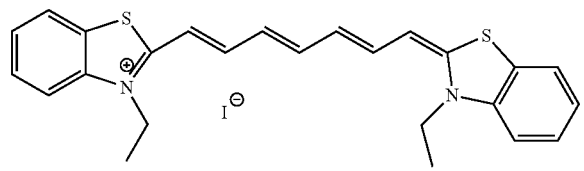 [SMILES: CCN1\C(=C/C=C/C=C/C=C/c2sc3ccccc3[n+]2CC)Sc2ccccc21 ; [I-]]

and pharmaceutically acceptable salts thereof.

In certain aspects, the molecular probe includes a compound having the formula:

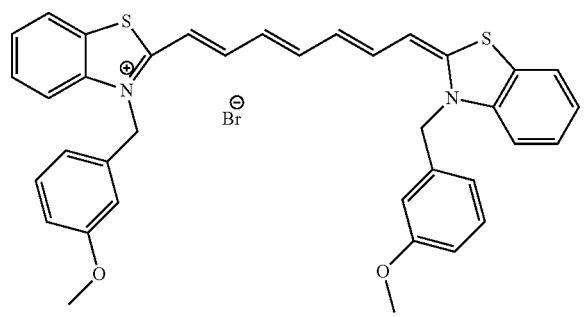 [SMILES: COc1cccc(CN2\C(=C/C=C/C=C/C=C/c3sc4ccccc4[n+]3Cc3cccc(OC)c3)Sc3ccccc32)c1 ; [Br-]]

and pharmaceutically acceptable salts thereof.

In some aspects, the myelination related disorder includes a neurodegenerative autoimmune disease. In certain aspects, the neurodegenerative disease can be multiple sclerosis.

In some aspects, the distribution and/or amount of the molecular probe in the neural tissue can be measured using an in vivo imaging modality. The in vivo imaging modality can include a near-infrared fluorescence imaging modality. In some aspects, the in vivo imaging modality can include a fluorescence tomography imaging modality. In other aspects, the molecular probe can be administered parenterally. In some aspects, the subject can include a mammal, such as a human.

The application further relates to a method of monitoring the efficacy of a remyelination therapy in a subject. The method includes administering to a subject undergoing remyelination therapy a molecular probe that includes a compound having a general formula selected from the group consisting of:

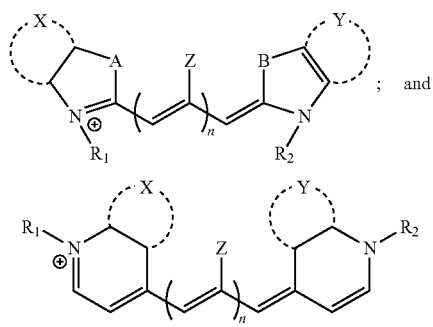

; and wherein n is an integer from 1 to 10; A, B each independently represent $CR'_2$, O, S, NH, $CH_2CH_2$, CH=CH; $R_1$, $R_2$, R', and Z each independently represent H, alkyl, alkenyl, alkynyl and/or an aryl group; X and Y each independently represent

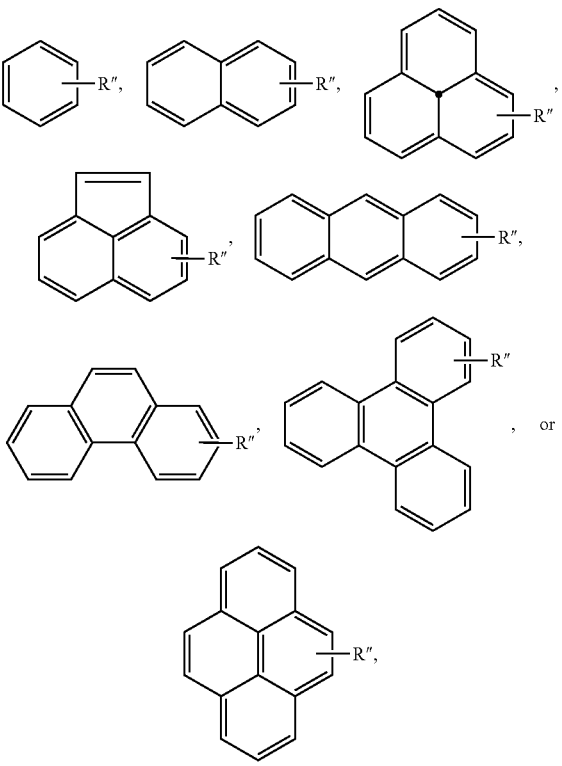

, or wherein R''=H, alkyl, alkenyl, alkynyl or an aryl group; and pharmaceutically acceptable salts thereof. The distribution and/or amount of the molecular probe bound to and/or labeling myelin in the subject's neural tissue is detected, measured, and/or quantified and compared to a control. An increased distribution and/or amount of the molecular probe compared to the control is indicative of efficacy of the remyelination therapy.

In some aspects of the invention, $R_1$=$R_2$. In some aspects, A=B. In some aspects, X=Y. In other aspects, n is an integer from 3 to 10.

In some aspects, the molecular probe can include an additional imaging moiety that allows the molecular probe to be detected by more than one imaging modality. In some embodiments the imaging moiety can include a radiolabel that is conjugated to the molecular probe. The radiolabel can be selected from the group consisting of C-11, F-18, I-124, I-123, I-131, and Tc-99m. In some aspects, the imaging moiety that is conjugated to the molecular probe can include a magnetic resonance contrast agent allows the molecular probe to be viewed by magnetic resonance imaging. The magnetic resonance contrast agent can include, for example, a chelating agent, gadolinium, or F-19 that is bound to the molecular probe to facilitate or enhance magnetic resonance imaging.

In certain aspects, the molecular probe includes a compound having the formula:

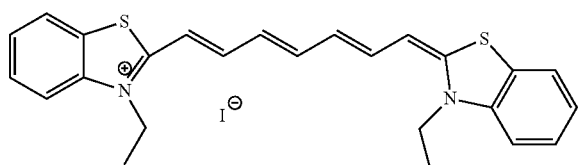

and pharmaceutically acceptable salts thereof.

In certain aspects, the molecular probe includes a compound having the formula:

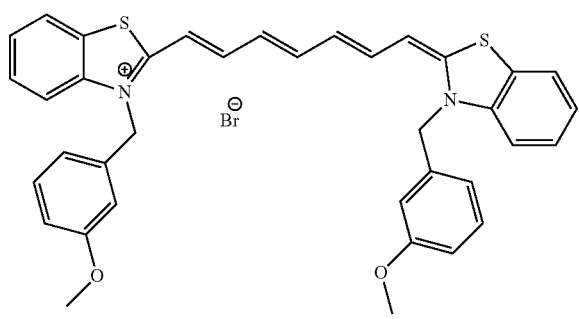 [SMILES: COc1cccc(CN2\C(=C/C=C/C=C/C=C/c3sc4ccccc4[n+]3Cc3cccc(OC)c3)Sc3ccccc32)c1 ; [Br-]]

and pharmaceutically acceptable salts thereof.

In some aspects, the distribution and/or amount of the molecular probe in the neural tissue can be measured using an in vivo imaging modality. The in vivo imaging modality can include a near-infrared fluorescence imaging modality. In some aspects, the in vivo imaging modality can include a fluorescence tomography imaging modality. In other aspects, the molecular probe can be administered parenterally. In some aspects, the subject can include a mammal, such as a human.

The application further relates to a method of screening the myelination effects of an agent. The method includes administering an agent to the subject and then administering a molecular probe that includes a compound having a general formula selected from the group consisting of:

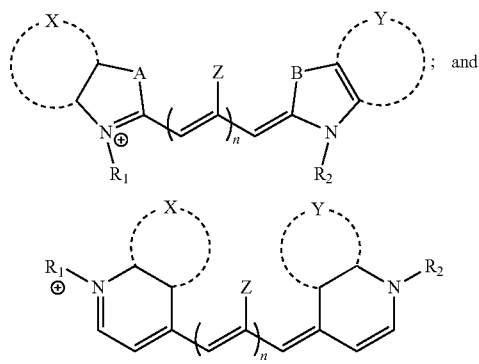

wherein n is an integer from 1 to 10; A, B each independently represent $CR'_2$, O, S, NH, $CH_2CH_2$, CH=CH; $R_1$, $R_2$, R', and Z each independently represent H, alkyl, alkenyl, alkynyl and/or an aryl group; X and Y each independently represent

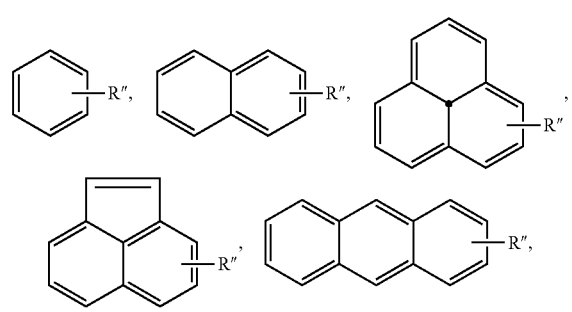

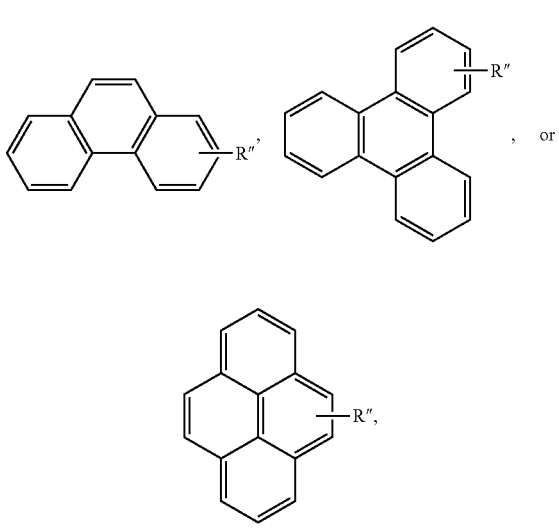

wherein R''=H, alkyl, alkenyl, alkynyl or an aryl group; and pharmaceutically acceptable salts thereof. The distribution and/or amount of the molecular probe bound to and/or labeling myelin in the subject's neural tissue is detected, measured, and/or quantified and compared to a control. An increased distribution and/or amount of the molecular probe compared to the control is indicative of the agent increasing myelination of the neural tissue of the subject. A decreased distribution and/or amount of the molecular probe compared to the control is indicative of the agent decreasing myelination of the subject of the neural tissue of the subject.

In some aspects, $R_1=R_2$. In some aspects, A=B. In some aspects, X=Y. In other aspects, n is an integer from 3 to 10.

In some aspects, the molecular probe can include an additional imaging moiety that allows the molecular probe to be detected by more than one imaging modality. In some embodiments the imaging moiety can include a radiolabel that is conjugated to the molecular probe. The radiolabel can be selected from the group consisting of C-11, F-18, I-124, I-123, I-131, and Tc-99m. In some aspects, the imaging moiety that is conjugated to the molecular probe can include a magnetic resonance contrast agent allows the molecular probe to be viewed by magnetic resonance imaging. The magnetic resonance contrast agent can include, for example, a chelating agent, gadolinium, or F-19 that is bound to the molecular probe to facilitate or enhance magnetic resonance imaging.

In certain aspects, the molecular probe includes a compound having the formula:

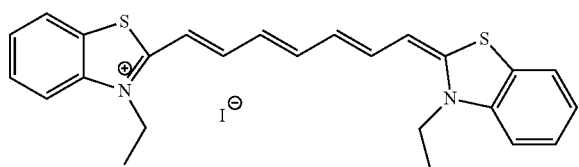

and pharmaceutically acceptable salts thereof.

In certain aspects, the molecular probe includes a compound having the formula:

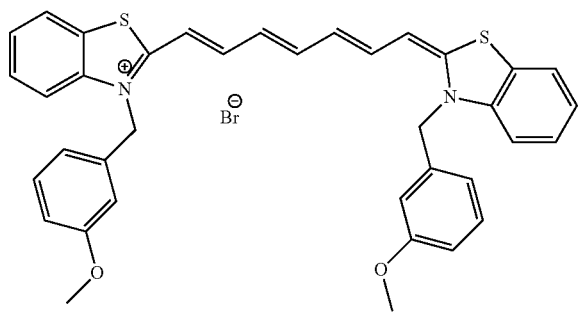 [SMILES: COc1cccc(CN2\C(=C/C=C/C=C/C=C/c3sc4ccccc4[n+]3Cc3cccc(OC)c3)Sc3ccccc32)c1 ; [Br-]]

and pharmaceutically acceptable salts thereof.

BRIEF DESCRIPTION OF THE DRAWINGS

The foregoing and other features and advantages described herein will become apparent to those skilled in the art to which the present invention relates upon reading the following description with reference to the accompanying drawings, in which:

FIG. 1 illustrates plots showing (A) the excitation and emission spectra of CNIR (100 nM in DMSO); (Excitation spectra: emission at 797 nm (range 600-850 nm), maximal excitation wavelength at 782 nm. Emission spectra: excitation at 782 nm (range 600-850 nm), maximal emission wavelength at 797 nm); and (B) the excitation and emission spectra of CNP (100 nM in DMSO). (Excitation spectra: emission at 691 nm (range 600-850 nm), maximal excitation wavelength at 673 nm. Emission spectra: excitation at 673 nm (range 600-850 nm), maximal emission wavelength at 691 nm.)

FIG. 2 illustrates images showing (A) in vitro chemical staining of free floating brain sections from wild-type mice with CNIR (1 µM); (B) in vitro immunohistochemical staining of free floating brain sections from wild-type mice with myelin-specific antibody; (C) in vitro chemical staining of fresh frozen brain sections from wild-type mice with CNP (100 µM); and (D) in vitro immunohistochemical staining of fresh frozen brain sections from wild-type mice with myelin-specific antibody. Scale Bar: C, D=500 µm.

FIG. 3 illustrates (A) an X-ray image and (B) a fluorescent image of a living wild-type mouse from KODAK In-Vivo Multispectral System FX. The precise overlay image without fiduciary markers is shown in C.

FIG. 4 illustrates near-infrared fluorescence in vivo imaging in (A) Plp-Akt-DD mice and (B) wild-type mice recorded at 0, 2, 4, 6, 8, 10, 15, 20, 25, 30 min after the i.v. injection of CNIR 0.1 mg/kg.

FIG. 8 illustrates (A) schematic drawing showing the design of hybrid myelin imaging probe for near infrared fluorescence imaging and positron emission tomography; and (B) the synthesis route of CNP and its precursor, CNP0. Reagents and conditions (a) 100° C., 10 h; (b) 90° C., 12 h; (c) $Ac_2O$, DIPEA, AcONa, DCM/Acetonitrile, reflux, 30 min; (d) AcOH, $Ac_2O$, 140° C., 1 h; (e) AcONa, DCM/Acetonitrile, reflux, 30 min.

FIG. 9 illustrates (A) the structure of 3-(3-methoxyphenethyl)-2-((1E,3E,5E,7Z)-7-(3-(3-methoxyphenethyl)benzo[d]thiazol-2(3H)-ylidene)hepta-1,3,5-trien-1-yl)benzo[d]thiazol-3-ium bromide (CNP); (B) the excitation and emission spectra of CNP (100 nM in DMSO). Excitation spectra: emission at 804 nm (range 650-900 nm), maximal excitation wavelength at 786 nm. Emission spectra: excitation at 786 nm (range 650-900 nm), maximal emission wavelength at 804 nm. In vitro immunohistochemical staining of fresh frozen brain tissue sections of wild-type mice (C) and shiverer mice (D) with MBP antibody. In vitro CNP staining (1 mM) of fresh frozen brain tissue sections of wild-type mice (E) and shiverer mice (F). In vitro CNP staining of myelinated regions and subsequent co-staining of MBP antibodies and MAP2. (G) CNP staining of both myelin tracts and granule layers present in cerebellum, which significantly blocks antibody staining of MBP (H) in the same section (I). (J) CNP staining of small myelin fibers present in frontal cortex, which also significantly blocks antibody staining of MBP (K) in the same section (L). (M) CNP staining of compact myelin fibers present in caudate putamen, which significantly blocks antibody staining of MBP(N) in the same section (O). Inhibition of immunohistochemical staining by CNP indicates that CNP stains myelin through specific binding to MBP. Scale bar: C-F, J-L=50 µm, G, H, I=200 µm.

FIG. 10 illustrates near-infrared fluorescence in vivo imaging in (A) wild-type mice and (B) shiverer mice recorded at pre-injection, 5, 10, 15, 20, 25, 30, 40, 50 and 60 min after i.v. injection of CNP 0.1 mg/kg.

FIG. 11 illustrates plots showing the quantification of in vivo imaging of the myelin sheath in the living mice of: (A) the average radiance of wild-type mice after the injection of CNP and vehicle at 0, 5, 10, 15, 20, 25, 30, 40, 50, 60, 70, 80, 90 min(P<0.0001, two-tailed t-test, CI 99%); (B) the average radiance of shiverer mice after the injection of CNP and vehicle at 0, 5, 10, 15, 20, 25, 30, 40, 50, 60, 70, 80, 90 min (P<0.0001, two-tailed t-test, CI 99%); and (C) the comparison of the average radiance between the shiverer mice and wild-type mice after deducting the vehicle signals (P=0.0002, two-tailed t-test, CI 99%). Values are given as mean±SEM.

FIG. 12 illustrates near-infrared fluorescence in vivo imaging in (A) saline-rats and (B) LPC-rats recorded at pre-injection, 10, 20, 30, 40, 50, 60, 70, 80 and 90 min after i.v. injection of CNP 0.1 mg/kg. The quantification of in vivo imaging of the myelin sheath in the living rats. (C) The comparison of the avg radiance between the saline-rats (blue) and LPC-rats (red) after deducting the control signals at 0, 5, 10, 15, 20, 25, 30, 35, 40, 45, 50, 55, 60, 65, 70, 75, 80, 85 and 90 min (P=0.045, two-tailed t-test, CI 99%). Values are given as mean±SEM. After imaging, the rats were killed, and then the brain sections stained with Black-Gold II and CNP. The results indicate that CNP can detect the LPC induced demyelination lesion on CNS in vitro, also matched the in vivo NIRF imaging results. CNP (D) and Black-Gold II (F) staining on saline-rats brain sections show the injection site on the brain and there is no lesion was found, CNP (E) and Black-Gold II (G) staining on LPC-rats brain sections show the lesion induced by the LPC injection. Scale bar=50 µm.

DETAILED DESCRIPTION

Figure 5:
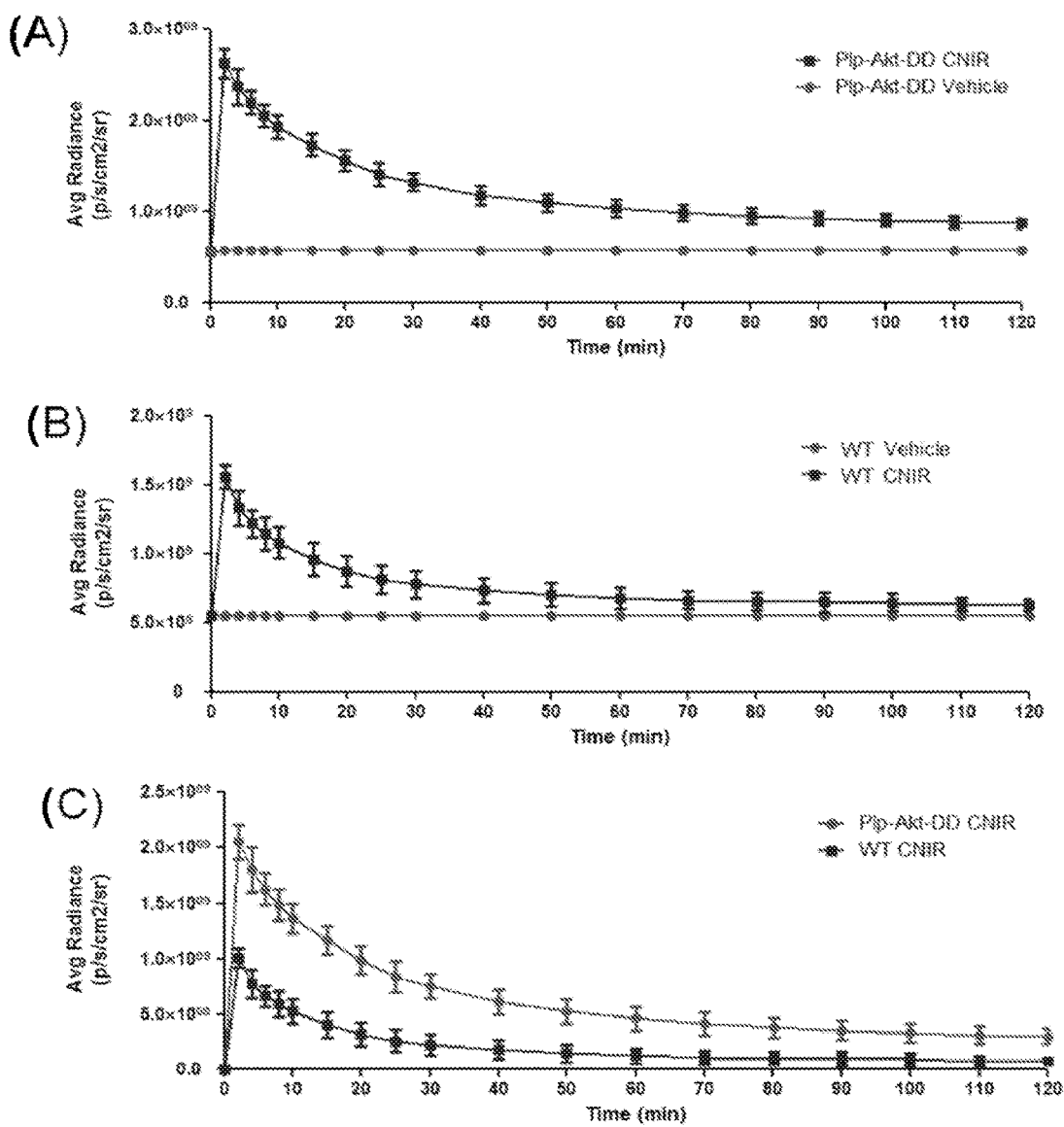
FIG. 5 illustrates plots showing the quantification of in vivo imaging of the myelin sheath in living mice of: (A) the avg radiance of Plp-Akt-DD mice after the injection of CNIR and vehicle at 0, 2, 4, 6, 8, 10, 15, 20, 25, 30, 40, 50, 60, 70, 80, 90, 100, 110, 120 min(P<0.0001, two-tailed t-test, CI 99%), (B) the avg radiance of wild-type mice after the injection of CNIR and vehicle at 0, 2, 4, 6, 8, 10, 15, 20, 25, 30, 40, 50, 60, 70, 80, 90, 100, 110, 120 min(P<0.0001, two-tailed t-test, CI 99%), and (C) the comparison of the avg radiance between the Plp-Akt-DD mice and wild-type mice after deducting the vehicle signals (P=0.0012, two-tailed t-test, CI 99%). Values are given as mean±SD.

The definitions provided herein are to facilitate understanding of certain terms used frequently herein and are not meant to limit the scope of the application.

As used herein, the term "pharmaceutically acceptable" refers to a material that is not biologically or otherwise undesirable, i.e., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug administration. "Pharmacologically active" (or simply "active") as in a "pharmacologically active" derivative or analog, refers to a derivative or analog having the same type of pharmacological activity as the parent compound and approximately equivalent in degree.

As used herein, the term "pharmaceutically acceptable salts" or complexes refers to salts or complexes that retain the desired biological activity of the parent compound and exhibit minimal, if any, undesired toxicological effects. Non-limiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, palmoic acid, alginic acid, polyglutamic acid, naphthalenesulfonic acids, naphthalenedisulfonic acids, and polygalacturonic acid; (b) base addition salts formed with cations such as sodium, potassium, zinc, calcium, bismuth, barium, magnesium, aluminum, copper, cobalt, nickel, cadmium, sodium, potassium, and the like, or with an organic cation formed from N,N-dibenzylethylene-diamine, ammonium, or ethylenediamine; or (c) combinations of (a) and (b); e.g., a zinc tannate salt or the like.

As used herein, a molecular probe exhibits "specific binding" or "selective binding" to myelin if it associates more frequently with, more rapidly with, for a longer duration with, or with greater affinity to, myelin than with tissues not containing myelin. "Non-specific binding" refers to binding of the molecular probe to non-myelin containing tissue. For relative binding values, such as specific binding or nonspecific binding, each sample should be measured under similar physical conditions (i.e., temperature, pH, and solvent). Generally, specific binding is characterized by a relatively high affinity of a molecular probe to a receptor and a relatively low to moderate capacity. Typically, binding is considered specific when the affinity constant Ka is at least $10^6$ M$^{-1}$. A higher affinity constant indicates greater affinity, and thus typically greater specificity. "Non-specific" binding usually has a low affinity with a moderate to high capacity. Non-specific binding usually occurs when the affinity constant is below $10^6$M$^{-1}$.

As used herein, the phrase "parenteral administration" refers to any means of introducing a substance or compound into a subject, that does not involve oral ingestion or direct introduction to the gastrointestinal tract, including but not limited to subcutaneous injection, intraperitoneal injection, intramuscular injection, intravenous injection, intrathecal injection, intracerebral injection, intracerebroventricular injection, or intraspinal injection, or any combination thereof.

As used herein, the phrase "remyelination" refers to the spontaneous, therapeutic, or experimentally induced repair, regeneration, or otherwise enhanced constitution or functionality of the insulating material ensheathing neuronal axons.

As used herein, the phrase "molecular imaging" refers to a non-invasive technique for in vivo imaging of biological targets at molecular level. Molecular imaging can involve the targeting of a biomarker with a molecular probe.

As used herein, the phrase "molecular probe" refers to a compound that specifically binds to a biomarker (e.g., myelin), allowing for the imaging and studying of the marker. As used herein, the phrase "biomarker" refers to a biological substance that is specific to a certain biological process or mechanism.

As used herein, the term "subject" refers to an animal, such as a mammal including a small mammal (e.g., mouse, rat, rabbit, or cat) or a larger mammal (e.g., dog, pig, or human). In particular aspects, the subject is a large mammal, such as a human.

As used herein, the terms "control" or "control sample" refer to one or more biological samples isolated from an individual or group of individuals that are normal (i.e., healthy). The term "control", "control value" or "control sample" can also refer to the compilation of data derived from samples of one or more individuals classified as normal, one or more individuals diagnosed with a myelination related disease.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

This application relates to molecular probes that upon administration to a subject can specifically or selectively bind to, localize with, and/or label myelinated regions of the nervous system, including the central nervous system and peripheral nervous system, and upon specifically or selectively binding to, localizing with, and/or labeling can be imaged, using, for example, fluorescence or near-infrared imaging techniques, to detect, measure, and/or quantify the amount, level, and/or distribution of myelin in the tissue being imaged. The molecular probes described herein can be used in a method of detecting a level of myelination in vivo in a subject, a method of detecting a myelination related disorder in a subject, a method of monitoring the remyelination effects of an agent in a subject, a method of screening the myelination effects of an agent in a subject, surgical methods where the presence or location of nerves is desired, and multi-modal imaging applications of myelin.

In an embodiment of the application, the molecular molecular probes can exhibit emission/excitation wavelengths in a range between about 650 nm and about 900 nm. Thus, the molecular probes can be used in a method for irradiating and imaging myelin with light of the wavelength range from about 650 to about 900 nm in the near-infrared (NIR) region. For example, a molecular probe described herein can have excitation peaked at about 782 nm and emission peaked at about 797 nm. It is contemplated that the emitting light of these probes can advantageously penetrate tissue, such as whole brain tissue and the skull plates of a subject, to allow for in vivo imaging during surgical procedures.

In other embodiments, the molecular probes described herein may have high quantum yield, high molar absorptivity, large Stokes shifts (e.g., about 15 nm), large two-photon excitation cross-sections as well as short lifetimes (e.g., about 1 ns) to increase the sensitivity of the probes. In some aspects, the molecular probes can meet the requirements that generally apply to diagnostic pharmaceuticals. As these substances may be applied at higher doses and for a longer diagnostic period, they can have a low-toxicity. In addition, the molecular probes described herein can be of low molecular weight, lipophilic, and readily penetrate the blood-brain barrier in sufficient amounts to be detectable by near-infrared radiation and bind to myelin fibers with high affinity and specificity without being rapidly degraded. The molecular probes are also sufficiently stable in chemical and photophysical respect, at least for as long as the diagnostic period lasts.

In some embodiments of the application, the molecular probe can include a compound having the general formula selected from the group consisting of:

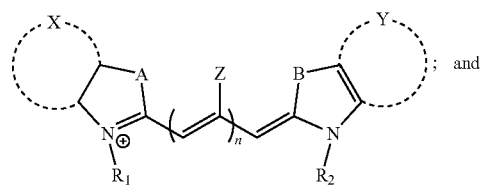; and

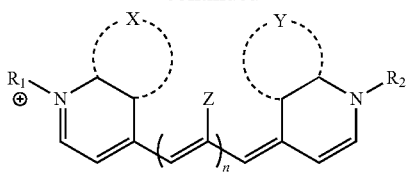

wherein n is an integer from 1 to 10; A, B each independently represent $CR'_2$, O, S, NH, $CH_2CH_2$, CH=CH; $R_1$, $R_2$, R', and Z each independently represent H, alkyl, alkenyl, alkynyl and/or an aryl group; X and Y each independently represent

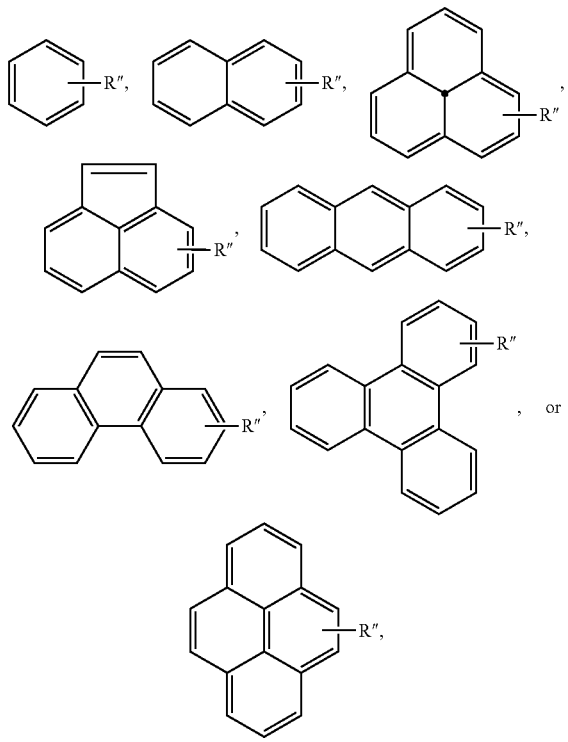

wherein R''=H, alkyl, alkenyl, alkynyl or an aryl group; and pharmaceutically acceptable salts thereof.

In some aspects of the invention, $R_1$=$R_2$. In some aspects, A=B. In some aspects X=Y. In another aspect, n is an integer from 3 to 10.

In other embodiments, the molecular probe can include 3,3'Diethylthiatricarbocyanine iodide (CNIR), which has the following formula:

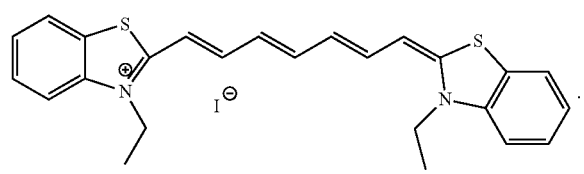 [SMILES: CCN1\C(=C/C=C/C=C/C=C/c2sc3ccccc3[n+]2CC)Sc2ccccc21 ; [I-]]

In still other embodiments, the molecular probe can include 3,3'-Di(2-meoxylbenzyl)-thiatricarbocyanine bromide (CNP), which has the following formula:

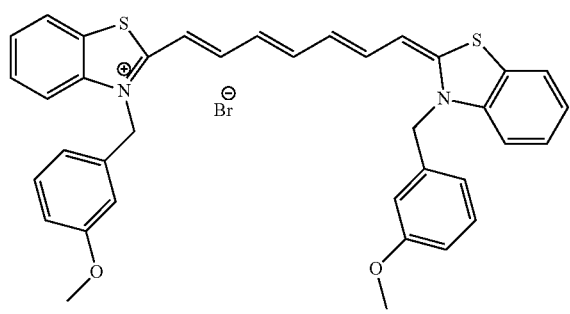

It will be appreciated that the compounds described herein are intended to include all isotopes of atoms of the compounds. Isotopes include those atoms having the same atomic number but different mass numbers. By way of example, isotopes of hydrogen include tritium and deuterium, and isotopes of carbon include C-13 and C-14.

The compounds described herein can have asymmetric centers. Compounds described herein containing an asymmetrically substituted atom can be isolated in optically active or racemic forms. It is well known in the art how to prepare optically active forms, such as by resolution of racemic forms or by synthesis from optically active starting materials. Many geometric isomers of olefins, C═N double bonds, and the like can also be present in the compounds described herein, and all such stable isomers are contemplated in the present invention. Cis and trans geometric isomers of the compounds of the present invention are described and can be isolated as a mixture of isomers or as separated isomeric forms. All chiral, diastereomeric, racemic, and geometric isomeric forms of a structure are intended, unless the specific stereochemistry or isomeric form is specifically indicated. All processes used to prepare compounds described herein and intermediates made therein are, where appropriate, considered to be part of the present invention. All tautomers of shown or described compounds are also, where appropriate, considered to be part of the present invention.

When a bond to a substituent is shown to cross a bond connecting two atoms in a ring, then such substituent can be bonded to any atom in the ring. When a substituent is listed without indicating the atom via which such substituent is bonded to the rest of the compound of a given formula, then such substituent can be bonded via any atom in such substituent. Combinations of substituents and/or variables are permissible, but only if such combinations result in stable compounds.

When an atom or a chemical moiety is followed by a subscripted numeric range (e.g., $C_{1-6}$), the invention is meant to encompass each number within the range as well as all intermediate ranges. For example, "$C_{1-6}$ alkyl" is meant to include alkyl groups with 1, 2, 3, 4, 5, 6, 1-6, 1-5, 1-4, 1-3, 1-2, 2-6, 2-5, 2-4, 2-3, 3-6, 3-5, 3-4, 4-6, 4-5, and 5-6 carbons.

As used herein, "alkyl" is intended to include unsubstituted and substituted branched (e.g., isopropyl, tert-butyl, isobutyl), straight-chain e.g., methyl, ethyl, propyl, butyl, pentyl, hexyl, heptyl, octyl, nonyl, decyl), and cycloalkyl (e.g., alicyclic) groups (e.g., cyclopropyl, cyclopentyl, cyclohexyl, cycloheptyl, cyclooctyl), alkyl substituted cycloalkyl groups, and cycloalkyl substituted alkyl groups. Such aliphatic hydrocarbon groups can have a specified number of carbon atoms. For example, $C_{1-6}$ alkyl is intended to include $C_1$, $C_2$, $C_3$, $C_4$, $C_5$, and $C_6$ alkyl groups. As used herein, "lower alkyl" refers to alkyl groups having from 1 to 6 carbon atoms in the backbone of the carbon chain. "Alkyl" further includes alkyl groups that have oxygen, nitrogen, sulfur or phosphorous atoms replacing one or more hydrocarbon backbone carbon atoms. In certain embodiments, a straight chain or branched chain alkyl has six or fewer carbon atoms in its backbone (e.g., $C_1$-$C_6$ for straight chain, $C_3$-$C_6$ for branched chain), for example four or fewer. Likewise, certain cycloalkyls have from three to eight carbon atoms in their ring structure, such as five or six carbons in the ring structure.

The term "substituted alkyls" refers to alkyl moieties having substituents replacing a hydrogen on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)).

As used herein, "alkenyl" is intended to include hydrocarbon chains of either straight or branched configuration having one or more carbon-carbon double bonds occurring at any stable point along the chain. For example, $C_{2-6}$ alkenyl is intended to include $C_2$, $C_3$, $C_4$, $C_5$, and $C_6$ alkenyl groups. Examples of alkenyl include, but are not limited to, ethenyl and propenyl.

As used herein, "alkynyl" is intended to include hydrocarbon chains of either straight or branched configuration having one or more carbon-carbon triple bonds occurring at any stable point along the chain. For example, $C_{2-6}$ alkynyl is intended to include $C_2$, $C_3$, $C_4$, $C_5$, and $C_6$ alkynyl groups. Examples of alkynyl include, but are not limited to, ethynyl and propynyl.

Furthermore, "alkyl", "alkenyl", and "alkynyl" are intended to include moieties, which are diradicals, i.e., having two points of attachment. A nonlimiting example of such an alkyl moiety that is a diradical is —$CH_2CH_2$—, i.e., a $C_2$ alkyl group that is covalently bonded via each terminal carbon atom to the remainder of the molecule.

"Aryl" includes groups with aromaticity, including 5- and 6-membered "unconjugated", or single-ring, aromatic groups that may include from zero to four heteroatoms, as well as "conjugated", or multicyclic, systems with at least one aromatic ring. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diaryl amino, and alkylaryl amino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl).

The terms "heterocyclyl" or "heterocyclic group" include closed ring structures, e.g., 3- to 10-, or 4- to 7-membered rings, which include one or more heteroatoms. "Heteroatom" includes atoms of any element other than carbon or hydrogen. Examples of heteroatoms include nitrogen, oxygen, sulfur and phosphorus.

Heterocyclyl groups can be saturated or unsaturated and include pyrrolidine, oxolane, thiolane, piperidine, piperazine, morpholine, lactones, lactams such as azetidinones and pyrrolidinones, sultams, and sultones. Heterocyclic groups such as pyrrole and furan can have aromatic character. They include fused ring structures such as quinoline and isoquinoline. Other examples of heterocyclic groups include pyridine and purine. The heterocyclic ring can be substituted at one or more positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety. Heterocyclic groups can also be substituted at one or more constituent atoms with, for example, a lower alkyl, a lower alkenyl, a lower alkoxy, a lower alkylthio, a lower alkylamino, a lower alkylcarboxyl, a nitro, a hydroxyl, —$CF_3$, or —CN, or the like.

The foregoing formulae represent the general structures of compounds found to be effective molecular probes for labeling myelin in vivo as well as in vitro as described in the examples below. As described above, they are characterized in part, by their ability upon parenteral or systemic administration to a subject to selectively localize in the myelinated regions via direct binding to or labeling of myelin membranes.

When referring to a compound described herein, it is intended that the term "compound" encompass not only the specified molecular probe entity but also its pharmaceutically acceptable, pharmacologically active analogs, including, but not limited to, salts, esters, amides, prodrugs, conjugates, active metabolites, and other such derivatives, analogs, and related compounds.

Typically, the molecular probe can be formulated into a pharmaceutical composition prior to use. When a composition described herein is applied to a subject, it is formulated to be compatible with its intended route of application. Examples of routes of application include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, DMSO, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid or cyclodextrin; buffers such as acetates, citrates or phosphates and agents for the adjustment of tonicity such as sodium chloride or dextrose. pH can be adjusted with acids or bases, such as hydrochloric acid or sodium hydroxide.

By way of example, CNIR can be provided in solution at a concentration of 1 μM, and CNP can be provided in solution at a concentration of 100 μM. A solution of CNIR or CNP can also contain saline, DMSO, and HCl. In some examples, a CNIR or CNP solution can include 0.05% DMSO/PBS (V/V). One skilled in the art can utilize CNIR and/or CNP with pharmaceutical carriers and/or excipients in varying concentrations and formulations depending on the desired use.

Compounds described herein can be produced as described in the Examples below. Work up of the reaction mixtures and purification of the compounds thus obtained may be carried out in accordance to known procedures. Acid addition salts may be produced from the free bases in known manner, and vice-versa. For example, the starting materials of 3,3'-Di(2-meoxylbenzyl)-thiatricarbocyanine bromide (CNP) are known and can be prepared according to methods known in the art or those disclosed in the Examples.

In some embodiments, the molecular probes described herein can be administered to a subject and utilized for labeling and detecting myelinated regions of a subject's nervous system (e.g., brain tissue). The molecular probe may be administered to the subject's nervous or neural tissue either in vivo or in vitro after a tissue sample has been removed from the body.

In some aspects, the molecular probes described herein can be used for the in vivo detection and localization of myelinated regions of a subject's nervous system. The molecular probe can be administered to the subject as per the examples contained herein, but typically through intravenous injection. "Administered", as used herein, means provision, introduction or delivery of a molecular probe described herein in an amount(s) and for a period of time(s) effective to label myelin in a subject's nervous system (e.g., brain tissue). The administration of a compound or composition described herein to a subject may be systemically or locally (e.g., to the subject's brain). For example, a molecular probe described herein may be administered to the subject such that it is delivered throughout the body.

In certain aspects, the molecular probe is administered systemically and crosses the blood brain barrier and binds to myelin in the subject's brain. In other aspects, the molecular probes described herein can be administered systemically for the in vivo detection and localization of myelinated regions of an animal's peripheral nervous system. Alternatively, the molecular probes described herein may be administered locally to a specific organ or tissue of interest. This local administration may be either in vivo in a living subject or in vitro after a tissue sample has been removed from the body.

Thus, one aspect of the application provides a method of detecting myelin in vivo in a subject's tissue by administering a molecular probe or pharmaceutical composition thereof to a subject. The amount of molecular probe needed to be detected can readily be determined by those skilled in the art. Increasing the amount of molecular probe and comparison to a suitable control can determine the precise dosage of the molecular probe needed. Dosage may be quite different depending on the purpose of application. The goal to be achieved is a detectable concentration of molecular probe in the tissue target region to be diagnosed. For example, a concentration of about 1 to about 100 µM in the brain tissue or in body fluids can be effective. The upper limit of dosage is only set by the tolerability of the respective substances and preparations.

In some embodiments, the molecular probes can be used in analytical, diagnostic, or prognostic applications related to myelin detection. For example, researchers studying normal brains can employ compounds and methods described herein to examine the morphology and distribution of myelinated tissue in a subject. The compounds and methods are also applicable in intraoperative nerve labeling, spinal imaging, non-invasive in vivo measurement of myelination levels, and preclinical and basic neuroscience bench research aimed at the study of the function and process of myelination, and the dysfunction and repair of myelin. In some embodiments, researchers studying normal nervous system tissue can employ this method to examine the morphology and distribution of myelinated tissue in an animal.

"Distribution" as used herein is the spatial property of being scattered about over an area or volume. In this case the "distribution of myelinated tissue" is the spatial property of myelin being scattered about over an area or volume included in the subject's nervous system tissue. Researchers interested in neurotoxicology and neuropathology can also use this method in several ways. One way is to infer demyelination by the absence of the molecular probe labeling compared to normal control tissue. A second way is to study morphological changes in the myelin such as a fragmented or beaded appearance of the myelin sheath.

In yet another embodiment, one skilled in the art can assess and quantify changes in myelin content in vivo. Myelin in a subject's tissue (e.g., brain) can be visualized and quantified using an in vivo imaging modality. For quantitative analysis, the fluorescence images are analyzed on a region of interest basis. The molecular probe may be visualized any time post administration depending on the application. In one example, at 2 min post administration, the fluorescence signals of the molecular probe in proportion to the myelin content in a subject's brain is recorded. In another example, fluorescence signals are recorded at about 2, 4, 6, 8, 10, 15, 20, 25, 30, 40, 50, 60, 70, 80, 90, 100, 110 and/or 120 min post-administration.

An in vivo imaging modality as used herein is an imaging modality capable of visualizing molecular probes described herein in vivo (within a living organism). After a compound or composition of the invention is administered, the compound is detected using an imaging modality. An exemplary in vivo imaging modality for use in the present invention can detect the fluorescence of the probe upon excitation with light, such as near-infrared light. One example of an imaging modality uses bioluminescence imaging. Another example of an in vivo imaging modality is fluorescent molecular tomography. Still other examples of imaging modalities include fluorescent microscopy, optical projection tomography (OPT), multispectral optoacoustic tomography (MSOT).

In some aspects, the molecular probes described herein can be detected in a subject using fluorescence imaging, where the energy from an external source of light, e.g., a laser, is absorbed and almost immediately re-emitted at a longer wavelength of lower energy. Since biological tissue has a relatively high permeability for long-wave light of the 600 to 1000 nm spectral region, both the detection of non-absorbed radiation in the form of a transmission visualization and the re-emitted fluorescence radiation can provide tissue-specific data. For example, a molecular probe described herein can be irradiated with light from the visible to the near infrared range of about 650 to about 900 nm Radiation that is not absorbed and fluorescence radiation are recorded separately or simultaneously, or against each other with a delay. A synthetic image is generated from the data obtained.

Fluorescent images can be generated and recorded using various methods. In some aspects, the tissue (e.g., a subject's brain tissue) is irradiated extensively, fluorescence information is visualized in local resolution by a charge-coupled device (CCD) camera, or where the tissue sectors to be imaged are scanned by a light ray concentrated in a fiber optical waveguide and signals obtained are converted into an image by computing.

The irradiation angle and the angle of observation can be selected from case to case to meet anatomic and optimum contrast requirements. The sensitivity of the method may be improved by subtracting the images prior to and after administering the molecular probe.

The measurement methods used are known to a person skilled in the art. The skilled artisan will also know what equipment parameters should be set to obtain optimum recording and evaluation conditions at given absorption or fluorescence wavelengths of the molecular probes used according to the invention.

In some aspects, the molecular probe can include an additional imaging moiety that allows the molecular probe to be detected by other imaging modalities, such PET imaging or magnetic resonance imaging. This allows the molecular probe to be used in a multi-modal imaging system and provide more sensitive and specific detection of myelin or myelination in tissue of a subject.

In one embodiment, the additional imaging moiety can include a radiolabel to aid in the detection of the molecular probe once it binds to myelin. A 'radiolabel' as used herein is any compound that has been joined with a radioactive substance. Examples of radiolabels include positron emitting $^{11}C$, $^{18}F$, $^{124}I$, $^{123}I$, $^{131}I$ and Tc-99m radiolabels. By way of example, a molecular probe that includes a radiolabel can include a compound having the following formula:

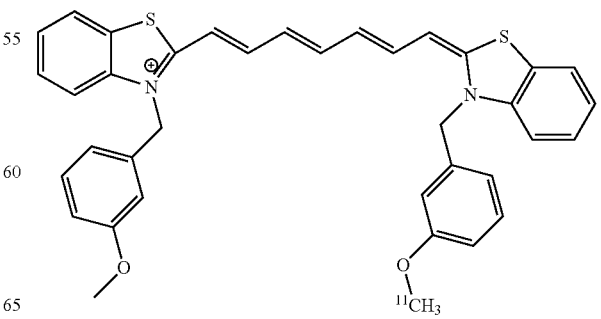

A molecular probe including a radio label can be detected in vivo using an imaging modality, such as positron emission tomography (PET) as well as by fluorescent imaging, such as near-infrared imaging. PET is a functional imaging technique that can detect chemical and metabolic change at the molecular level. Another example of an in vivo imaging modality that can be used to detect a molecular probe that includes a radio label is MicroPET. MicroPET is a high resolution positron emission tomography scanner designed for imaging small laboratory animals. In some aspects of the invention, the in vivo imaging modality is single-photon emission computerized tomography (SPECT).

In other embodiments, the additional imaging moiety can include a magnetic resonance contrast agent that is conjugated, coupled, or bound to an atom of the molecular probe and facilitates detection of the molecular probe by magnetic resonance imaging. In some aspects, the magnetic resonance contrast agent can include a chelating group, such as a Gd chelating ligand, or $^{19}F$ to improve the MRI contrast properties of the molecular probe. In one example, as disclosed in U.S. Pat. No. 7,351,401, which is herein incorporated by reference in its entirety, the chelating group can be of the form W-L or V—W-L, wherein V is selected from the group consisting of —COO—, —CO—, —CH$_2$O— and —CH$_2$NH—; W is —(CH$_2$)$_n$ where n=0, 1, 2, 3, 4, or 5; and L is:

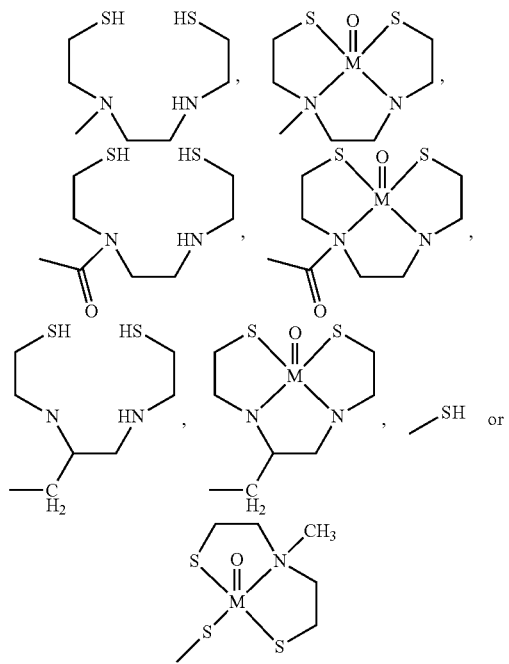

wherein M is selected from the group consisting of Tc and Re; or

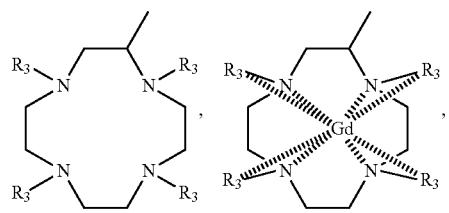

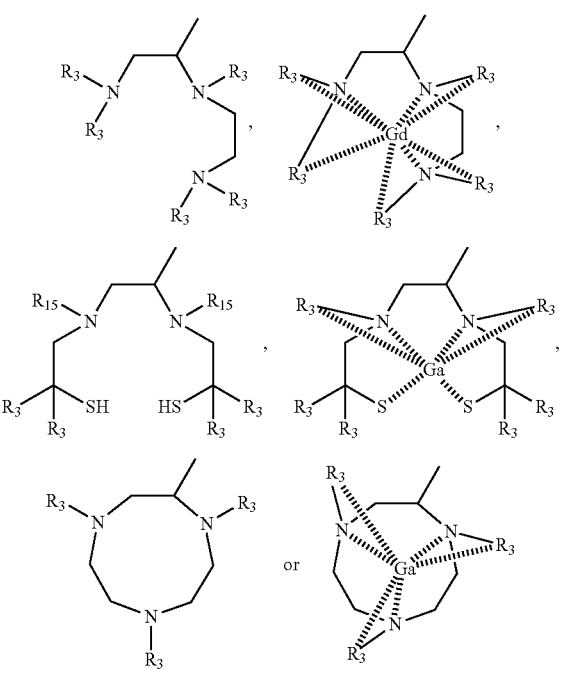

wherein each R$_3$ is independently is selected from one of:

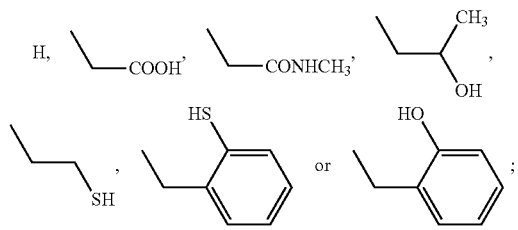

or a myelin binding, chelating compound (with or without a chelated metal group) or a water soluble, non-toxic salt thereof of the form:

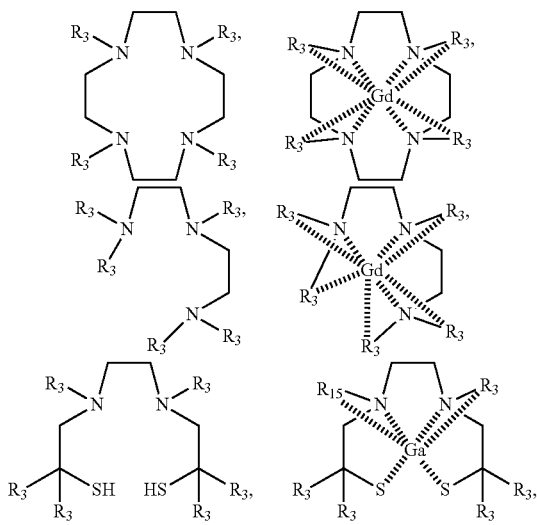

-continued

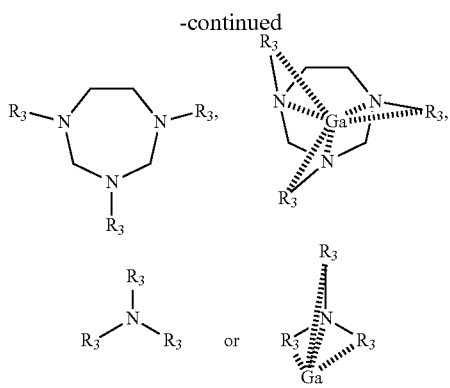

wherein each $R_3$ independently is selected from one of:

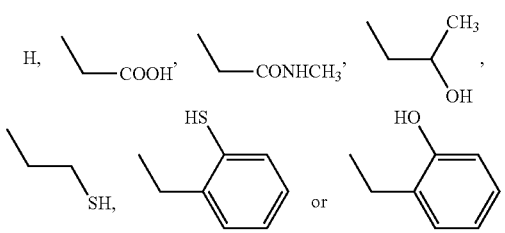

The chelating group can be coupled to at least one atom of the molecular prober through a carbon chain link. The carbon chain link can comprise, for example about 2 to about 10 methylene groups and have a formula of, for example, $(CH_2)_n$, wherein n=2 to 10.

The molecular probes described herein can readily penetrate the blood-brain bather (BBB) and directly bind to the myelinated white matter in proportion to the extent of myelination, which allows them to be used in monitoring myelin changes in the white matter of a subject. The molecular probes can also be used in combination with an in vivo imaging modality as imaging markers to directly assess the extent of total lesion volumes associated with demyelination. This can provide a direct clinical efficacy endpoint measure of myelin changes and identify effective therapies aimed at protection and repair of axonal damages.

The molecular probes can also be used to diagnose a myelination related disorder in a subject through the use of in vivo myelin labeling. Thus, in certain embodiments, pharmaceutical compositions containing the molecular probes describe herein can be used in the detection of myelination related disorders in a subject.

Methods of detecting a myelination related disorder include the steps of administering a molecular probe described herein to a subject. The distribution and/or amount of the molecular probe bound to and/or labeling myelin in the subject's neural tissue is then detected, measured, and/or quantified and compared to a control. A decreased distribution and/or amount of the molecular probe compared to the control is indicative of a decrease in myelination of the neural tissue and the presence of a myelination related disorder.

In one example, the methods described herein can be used to compare myelinated axonal regions of the brain in the normal tissues of control populations to those of a subject suspected of having a myelination disorder. If the suspect subject has a myelin related disorder, myelin may be virtually absent in lesioned areas thus indicating the presence of a myelin related disorder.

Myelination related disorders contemplated herein can include any disease, condition (e.g., those occurring from traumatic spinal cord injury and cerebral infarction), or disorder related to demyelination, remyelination, or dysmyelination in a subject. A myelin related disorder as used herein can arise from a myelination related disorder or demyelination resulting from a variety of neurotoxic insults. Demyelination is the act of demyelinating, or the loss of the myelin sheath insulating the nerves, and is the hallmark of some neurodegenerative autoimmune diseases, including multiple sclerosis, transverse myelitis, chronic inflammatory demyelinating polyneuropathy (CIDP), Guillain-Bane syndrome, Charcot-Marie-Tooth disease (CMT), anti-MAG peripheral neuropathy, leukodystrophies, diabetic neuropathy, chemotherapy induced neuropathy, or any combination thereof. In some embodiments, a myelination related disorder can include a demyelination related disorder of the peripheral nervous system, somatic nervous system, autonomic nervous system and/or the enteric nervous system. In other embodiments, a myelination related disorder can include a neurodegenerative autoimmune disease in a subject and more specifically, multiple sclerosis in a subject.

Another embodiment of the application, relates to a method of monitoring the efficacy of a remyelination therapy in a subject. The method includes administering a molecular probe to the subject. The distribution and/or amount of the molecular probe bound to and/or labeling myelin in the subject's neural tissue is detected, measured, and/or quantified and compared to a control. An increased distribution and/or amount of the molecular probe compared to the control is indicative of a efficacy of the remyelination therapy.

It is contemplated that the distribution and/or amount of molecular probe can be detected, measured, and/or quantified before, during, and after the course of a therapeutic regimen in order to determine the efficacy of the therapeutic regimen. One way to assess the efficacy of a remyelination therapy is to compare the distribution of the molecular probe before remyelination therapy with the distribution of the molecular probe after remyelination therapy has commenced or concluded.

Remyelination therapy as used herein refers to any therapy leading to a reduction in severity and/or frequency of symptoms, elimination of symptoms and/or underlying cause, prevention of the occurrence of symptoms and/or their underlying cause, and improvement or remediation of damage related to demyelination. For example, a remyelination therapy can include administration of a therapeutic agent, therapies for the promotion of endogenous myelin repair, or a cell based therapy (e.g., a stem-cell based therapy).

Another aspect of the application relates to methods for screening a myelination effects of an agent in a subject. The method includes administering an agent to the subject. The distribution and/or amount of the molecular probe bound to and/or labeling myelin in the subject's neural tissue is detected, measured, and/or quantified and compared to a control. An increased distribution and/or amount of the molecular probe compared to the control is indicative of agent increasing myelination of the subject. A decreased distribution and/or amount of the molecular probe compared to the control is indicative of agent decreasing myelination of the subject.

In some aspects of the present invention, the molecular probes described herein can be used to determine if an agent of interest has the potential to modulate demyelination, remyelination, or dysmyelination of axonal regions of an experimental subject's brain tissue.

The invention now being generally described, it will be more readily understood by reference to the following examples, which are included merely for purposes of illustration of certain aspects and embodiments of the present invention, and are not intended to limit the invention.

Example 1

We developed a series of myelin-imaging agents with different fluorescent properties. One type of these agents fluoresces in the near-infrared range with excitation and emission wavelengths above 650 nm. In this example we show the use of these near-infrared agents for in vivo optical imaging of myelination. For this purpose, we thoroughly studied myelin binding properties of 3, 3'Diethylthiatricarbocyanine iodide (CNIR) and 3,3'-Di(2-meoxylbenzyl)-thiatricarbocyanine bromide (CNP). CNP readily enters the brain and selectively binds to myelin fibers. The imaging sensitivity and specificity based on this probe were demonstrated in two animal models with different myelin loads.

Materials

CNIR and the chemicals used to synthesize CNP were purchased from Sigma-Aldrich, and CNP was synthesized following a reported method (See Zhang, Z., Berezin, M. Y., Kao, J. L. F., Avignon, A., Bai, M. and Achilefu, S, Near-Infrared Dichromic Fluorescent Carbocyanine Molecules. *Angew. Chem. Int. Ed.* 2008, 47, 3584-3587; Zhang, Z. and Achilefu, S. Design, synthesis and evaluation of near-infrared fluorescent pH indicators in a physiologically relevant range. *Chem. Commun.*, 2005, 5887-5889) prepared as described below. NMR spectra were recorded at 400 MHz in Varian instruments and are reported in ppm downfield from Me4Si.

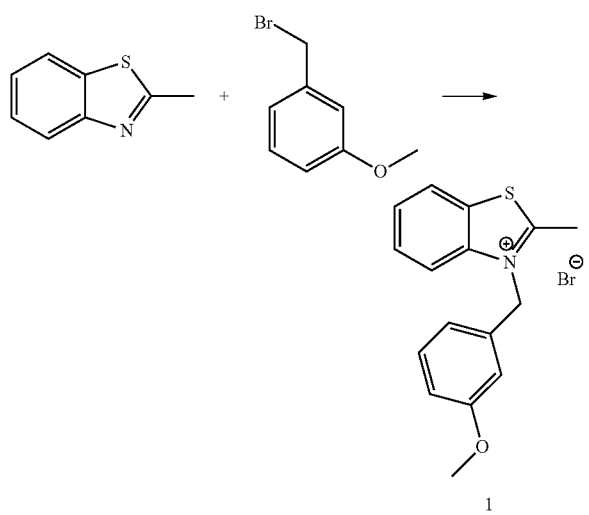

Synthesis of 3-(3-methoxybenzyl)-2-methylbenzo[d]thiazol-3-ium (1)

A solution of 2-methylbenzo[d]thiazole (5 g, 33.5 mmol) was added to a stirred solution of 1-(bromomethyl)-3-methoxybenzene (8.1 g, 40.2 mmol) at 90° C. The resultant mixture was heated for 30 min. The formed solid was collected recrystallized in acetonitrile to give 7.9 g (71%) of 1 as a white solid. $^1$H NMR (DMSO-$d_6$, 400 MHz): δ 8.46-8.48 (m, 1H), 8.15-8.17 (m, 1H), 7.76-7.83 (m, 2H), 7.26 (t, J=8.0 Hz, 1H), 6.92-6.94 (m, 2H), 6.84 (d, J=64 Hz, 1H), 6.02 (s, 2H), 3.71 (s, 3H), 3.23 (s, 3H). High resolution Mass calculated: 270.29471[M]$^+$; observed (ESI): 270.09478[M]$^+$.

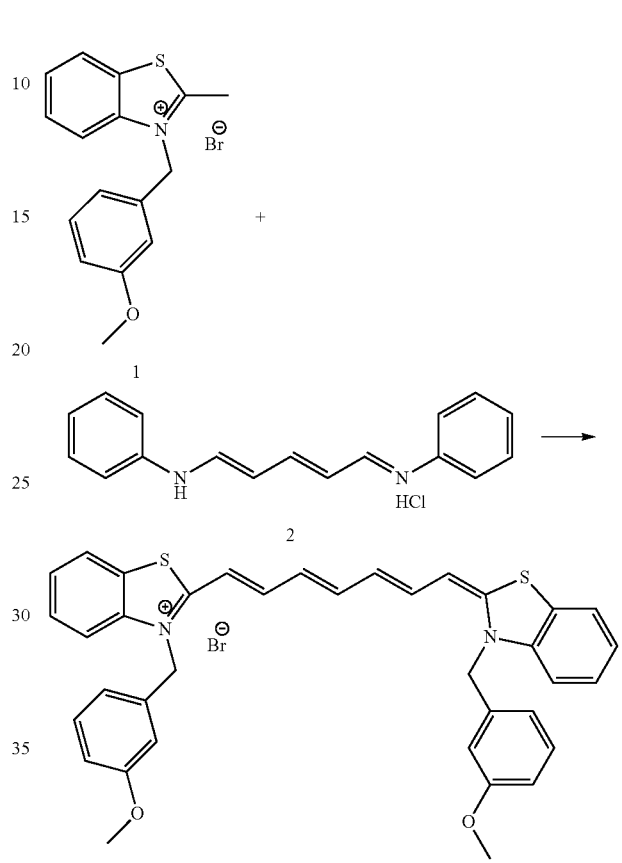

Synthesis of 3-(3-methoxybenzyl)-2-((1E,3E,5E,7E)-7-(3-(3-methoxybenzyl)benzo[d]thiazol-2(3H)-ylidene)hepta-1,3,5-trienyl)benzo[d]thiazol-3-ium (CNP)

Compound of 1 (5.4 g, 15.4 mmol) was added to a refluxing mixture of glutaconic adehyde dianiline hydrochloride (2.0 g, 7.0 mmol), Ac$_2$O (0.86 g, 8.4 mmol), DIPEA (2.4 mL, 14.0 mmol) and NaOAc (2.3 g, 28 mmol) in a mixed solvent of MeCN/DCM. The resultant mixture was stirred for additional 0.5 h. The solvent was removed by a rotary evaporator. The residue purified by column chromatography, then recrystallized in acetonitrile to afford 1.6 g (34%) of CNP as dark green solid. $^1$H NMR (DMSO-$d_6$, 400 MHz): δ 7.96-8.01 (m, 2H), 7.78 (t, J=12.0 Hz, 2H), 7.60-7.65 (m, 2H), 7.35-7.50 (m, 5H), 7.24 (t, J=8.0 Hz, 2H), 7.85-7.86 (m, 4H), 6.70 (d, J=8.0 Hz, 2H), 6.60 (d, J=12.0 Hz, 2H), 6.37 (t, J=12.0 Hz, 2H), 5.58 (s, 4H), 3.69 (s, 6H). High resolution Mass calculated: 601.19780W; observed (ESI): 601.19810[M]$^+$.

Methods

Animal Preparation

SWR/J mice were obtained from Harlan Laboratory, Oxford, Mich. The C57BL/6 mice and C3Fe.SWV-Mbp$^{shi}$/J shiverer mice were obtained from The Jackson Laboratory, Bar Harbor, Minn., and the Plp-Akt-DD transgenic mice were prepared as previously described (see Flores et al. 2008; Narayanan et al., 2009). Briefly, the transgenic mice expressing constitutively active Akt (HAAkt308D473D, Akt-DD) driven by the Plp promoter were generated and used as a hypermyelinated animal model. The Akt cDNA was inserted into the AscI/PacI sites of the modified Plp promoter cassette, and the Plp promoter/Akt-DD insert was injected into SJL/SWR F1 mice. Positive founders were identified by PCR amplification of tail DNA using IntronSV40F and Akt lower primer sequences. Analyses were done from litter-matched mice in all developmental experiments, and where possible with older animals. In all three lines, plp-Akt-DD9 was used.

Immunohistochemistry

For immunohistochemistry with free floating sections, mice were deeply anesthetized with isoflurane and perfused with PBS followed by 4% paraformaldehyde in PBS via the ascending aorta. Brains were dissected out, incubated for 24 hrs in 4% paraformaldehyde at 4° C., cryoprotected and sectioned (30 μm) with a sliding microtome. Free floating sections were immunostained overnight at 4° C. with rabbit anti-MBP antibody (Chemicon-Millipore, Bedford, Mass.) 1:2000 dilution in 3% normal goat serum in PBS, followed by one hour incubation at room temperature with IRDye 800CW Goat Anti-Rabbit (LI-COR Biosciences, Lincoln, Nebr.) 1:5000 dilution, then rinsed with PBS. The stained sections were covered with fluorescence mounting medium (VECTASHIELD, Vector Laboratories, Burlingame, Calif.). Images of the stained mouse brain sections were acquired on the Leica DM5000 inverted microscope (Y5 filter, BP 700/75).

CNIR Staining

Free floating sections were incubated in 1% $H_2O_2$/Triton-100 for 10 min, then incubated in a solution of CNIR (1 μM) in 1% DMSO/PBS for 30 min at room temperature. Washed three times with PBS before cover-slipping with fluorescence mounting medium (VECTASHIELD). Images were acquired on the LI-COR Odyssey infrared imaging system (LI-COR Biosciences, Lincoln, Nebr.).

CNP Staining

Fresh frozen sections were incubated in 1% Triton/1×PBS for 10 min, then incubated in a solution of CNP (100 μM) in 1% DMSO/PBS for 30 min at room temperature. Washed three times with 1×PBS before cover-slipping with fluorescence mounting medium (VECTASHIELD). Images of the stained mouse brain sections were acquired on the Leica DM5000 inverted microscope (L5 filter, BP 527/30).

Co-Registration of Fluorescent and X-Ray Images

The images were acquired with KODAK In-Vivo Multispectral System FX demonstration, (Carestream Health, Inc., Rochester, N.Y.). The fur of the mouse was shaved to avoid the problem of autofluorescence. 20 minutes after the i.v. injection of CNIR 0.1 mg/kg, the mouse was anesthetized utilizing isoflurane gas. The mouse was positioned on the center of the platen and imaged via fluorescence (ex 760 em 790) and X-ray. Vertical Resolution: 885 ppi, horizontal Resolution: 885 ppi.

Near-Infrared Fluorescence In Vivo Imaging

The in vivo Near-infrared fluorescence imaging was carried out using Xenogen IVIS Imaging System 200, (Caliper Life Science, Inc., Hopkinton, Mass.). To avoid the influence of the autofluorescence and light scattering due to the fur, all the mice were shaved before experiment. After the i.v. injection of CNIR 0.1 mg/kg, the mouse was anesthetized utilizing isoflurane gas, the mouse was positioned on the center of the stage (working temperature 20-40° C.). The Near-infrared images were acquired by Back-thinned, back-illuminated grade 1 CCD, which is thermoelectrically cooled to −90° C. ensuring low dark current and low noise. The fluorescent filter set for excitation was 705-780 nm, for emission was 810-885 nm. The experiments were controlled with Living Image 3.1 (Caliper Life Science. Inc., Hopkinton, Mass.). Lens: f/2. Field of view: 6.5 cm×6.5 cm. Imaging Pixels: 2048×2048. Exposure time: 0.5 s for all the images.

Quantification and Statistical Analysis

The near-infrared images were evaluated by Living Image 3.1 (Caliper Life Science. Inc., Hopkinton, Mass.). All the images used photon as the unit for the quantification, and the images were shown as overlaid photograph with fluorescence. Statistical analysis was performed using two-tailed t-test with GraphPad Prism 5, (GraphPad Software, Inc., La Jolla, Calif.).

Fluorescent Properties of CNIR and CNP

CNIR and CNP showed optimal NIRF properties that are suitable for in vivo imaging. The fluorescent excitation and emission spectrum is recorded using Varian fluorescent spectroscopy at the concentration of 100 nm in DMSO. As shown in FIG. 1, the excitation and emission maximum of CNIR are 782 nm and 797 nm, respectively and the excitation and emission maxima of CNP are 673 nm and 691 nm, respectively. Thus, both of these compounds exhibit excitation and emission properties that are located in the near infrared region (650 nm-900 nm).

In Vitro Binding Studies

The myelin-binding properties of CNIR and CNP were first examined by fluorescent tissue staining of wild-type mouse brain sections. For comparison, immunohistochemical staining with myelin-specific antibody was also conducted. At 1 μM concentration, CNIR selectively labeled intact myelin sheaths presented in the whole mouse brain, particularly in the corpus callosum and striatum (FIG. 2A). The pattern of myelin sheaths stained by CNIR was virtually identical to the pattern stained by MBP antibody (FIG. 2B). Similar results were observed with CNP (FIG. 2C, D). These observations indicated that CNIR and CNP bind specifically to myelin sheaths in vitro. In consideration of the fluorescent properties, CNIR has a longer maximum emission peak (797 nm) than CNP (691 nm), which can penetrate the tissue deeper than CNP; thus, we choose CNIR as the probe for further studies.

Brain Permeability

To determine the brain permeability of CNIR, we administered CNIR to wild-type mice through intravenous injection in tail vein. At 20 minutes post injection of CNIR (0.1 mg/kg), both X-ray and fluorescent images of the mouse brain were acquired using KODAK In-Vivo Multispectral System FX (FIG. 3). Co-registration of high quality X-ray image and fluorescent image confirmed that the strong fluorescence was indeed emitted from inside the brain. The results indicate that CNIR can readily penetrate the intact blood-brain barrier, making it a suitable NIR probe for in vivo studies.

In Vivo NIRF Imaging of Myelin

In vivo NIRF imaging was conducted in three mouse models that reflect different level of myelination in the brain. Female 3-month old Plp-Akt-DD mice (n=3) were used to represent hypermyelination in the brain. Age-matched Swiss Webster wild-type mice (n=2) were used to represent intact, normal myelination in the brain. Shiverer mice (C3Fe.SWV-Mbp$^{shi}$/J, n=2) were used to represent deficient myelination in the brain.

In Vivo NIRF Imaging in Hypermyelinated Mouse Model

CNIR (0.1 mg/kg) and vehicle (0.05% DMSO/PBS (V/V)) was first administered to the hypermyelinated mouse model through intravenous injected in the tail vein. The fluorescence signals were recorded at 2, 4, 6, 8, 10, 15, 20, 25, 30, 40, 50, 60, 70, 80, 90, 100, 110 and 120 min post injection. The images recorded at 2, 4, 6, 8, 10, 15, 20, 25, 30 min post injections are shown in FIG. 4. To exclude the influence of autofluorescence from the mouse tissues and impact from the solution, the vehicle (0.05% DMSO/PBS (V/V)) also injected and fluorescence was recorded at 2, 4, 6, 8, 10, 15, 20, 25, 30, 40, 50, 60, 70, 80, 90, 100, 110 and 120 min to compare with the CNIR solution (images not shown). The fluorescent radiance of Plp-Akt-DD mice is much stronger than that observed in the wild-type mice, which is consistent with the fact that the myelin content in the Plp-Akt-DD mice is much higher than that in the wild-type mice.

Quantitative analysis of these images was then conducted. As shown in FIG. 5, the average fluorescent intensity of CNIR in Plp-Akt-DD mice is higher than that observed wild-type mice. This is consistent with the enhanced myelin content in Plp-Akt-DD mice. The significant difference between the hypermyelinated and wild-type models appeared as early as 2 min post injection with much stronger fluorescent signal being detected in the hypermyelinated mouse brain, indicating fast brain entry of CNIR in proportion to the myelin content. Compared to the fast clearance of CNIR in WT control, relatively slower clearance was observed in the hypermyelinated mice. These results show the use of CNIR used as a probe for the in vivo near-infrared fluorescence imaging.

In Vivo NIRF Imaging in Shiverer Mouse Model

Figure 6:
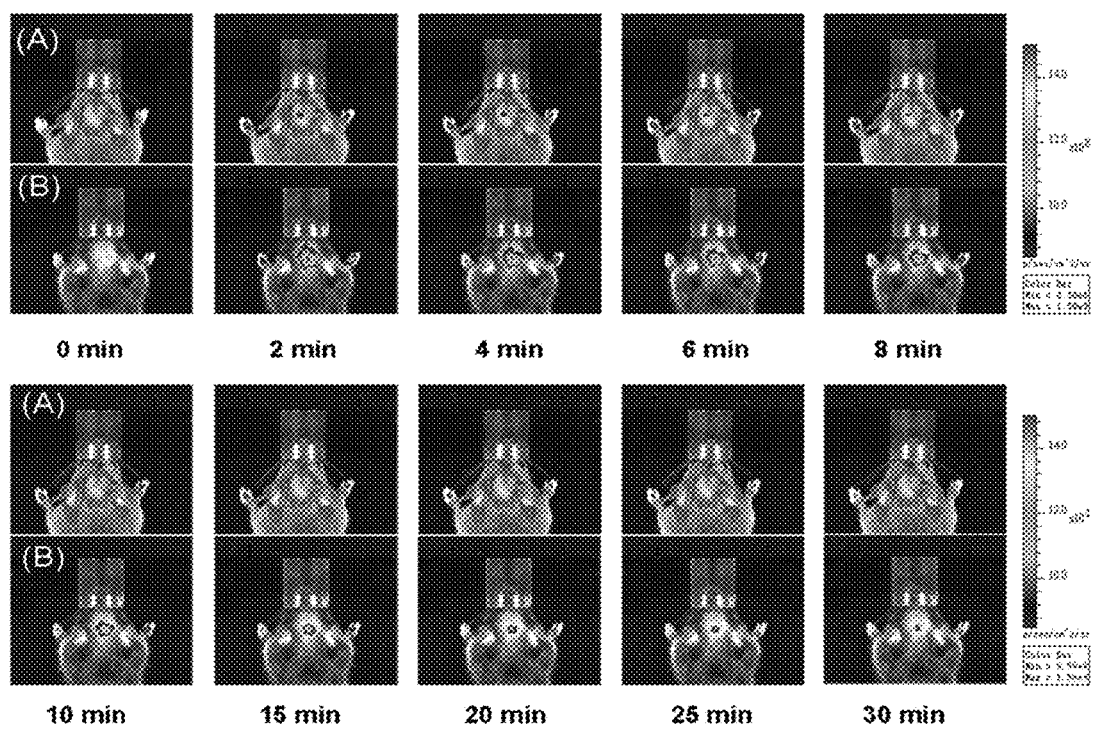
FIG. 6 illustrates near-infrared fluorescence in vivo imaging in (A) shiverer mice and (B) wild-type mice recorded at 0, 2, 4, 6, 8, 10, 15, 20, 25, 30 min after the i.v. injection of CNIR 0.1 mg/kg.

We then evaluated the pharmacokinetic profiles of CNIR in 3-month old female shiverer mice (n=3) and age-matched wild-type mice (n=2). The in vivo NIR imaging was conducted using the same dosage as in the hypermyelinated mouse model. The fluorescent signals were recorded at 2, 4, 6, 8, 10, 15, 20, 25, 30, 40, 50, 60, 70, 80, 90, 100, 110 and 120 min after i.v. injection of CNIR and the vehicle (0.05% DMSO/PBS (V/V)). As shown in FIG. 6, the fluorescent intensities in the brain between the two shiverer and wild-type models were significant different.

Figure 7:
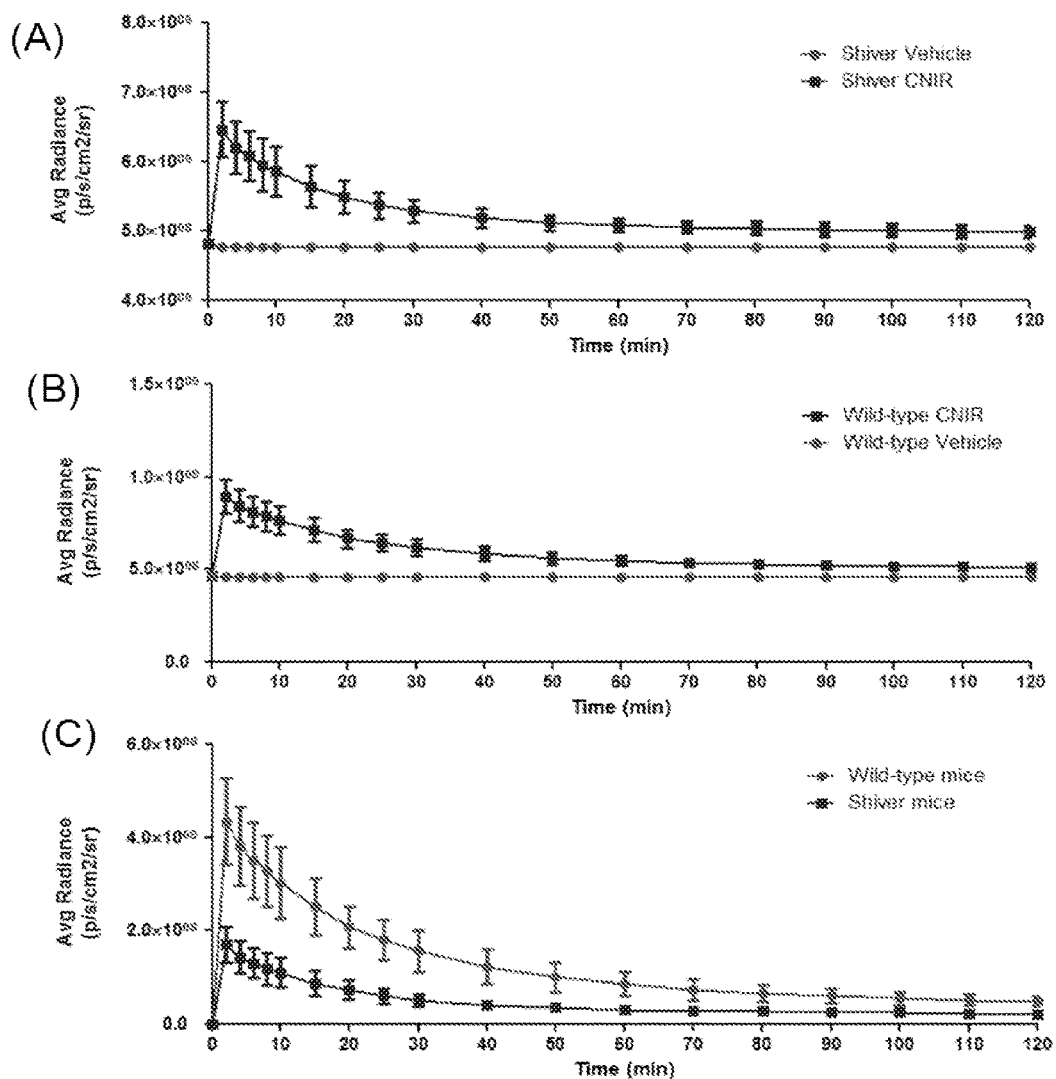
FIG. 7 illustrates plots showing the quantification of in vivo imaging of the myelin sheath in living mice of: (A) the avg radiance of shiverer mice after the injection of CNIR and vehicle at 0, 2, 4, 6, 8, 10, 15, 20, 25, 30, 40, 50, 60, 70, 80, 90, 100, 110, 120 min (P<0.0001, two-tailed t-test, CI 99%); (B) the avg radiance of wild-type mice after the injection of CNIR and vehicle at 0, 2, 4, 6, 8, 10, 15, 20, 25, 30, 40, 50, 60, 70, 80, 90, 100, 110, 120 min(P<0.0001, two-tailed t-test, CI 99%); and (C) the comparison of the avg radiance between the shiverer mice and wild-type mice after deducting the vehicle signals (P=0.0019, two-tailed t-test, CI 99%). Values are given as mean±SD.

Based on these images, quantitative analyses were conducted to determine the time course of fluorescent radiance. As shown in FIG. 7, the average radiance at 30 minutes in wild-type mice is eightfold greater than that observed in shiverer mice. Since the shiverer mice are deficient in CNS myelin, the fluorescent signal originated from the shiverer mice is very weak, even at its peak at 2 min. These results further demonstrated that accumulation of CNIR in the brain is proportional to the myelin content and can be used as a surrogate marker of myelination.

Example 2

Hybrid Probe for Molecular Neuroimaging In Vivo

In this example, we designed and developed a novel hybrid positron emission tomography and near-infrared fluorescence (PET-NIRF) probe (FIG. 8A) for myelin detection. The imaging sensitivity and specificity based on this probe were demonstrated in a hypomyelination animal model. Complementing the existing myelin imaging modalities, CNP can provide both absolute quantification information (PET) and relative quantification information (NIRF), it also can be used as a powerful tool for in vivo studies in the preclinical screening and development of drugs.

Materials and Methods

All animal experiments were performed in accordance with guidelines approved by the Institutional Animal Care and Use Committee of Case Western Reserve University (Protocol 2010-0007). The animals were subjected to minimal stress during tail vein injections. All chemicals were obtained from Sigma-Aldrich (Milwaukee, Wis.), TCI America (Portland, Oreg.) and used without further purification.

Synthesis

The synthetic route was shown in FIG. 8B. Briefly, the CNP and CNP0 were synthesized by coupling glutaconic aldehyde dianiline hydrochloride with 1 and ⅓, respectively. The synthesis and analytic data were shown in supporting information.

Physical Properties

The excitation and emission spectra of CNP were recorded using Cary Eclipse Fluorescence Spectrophotometers (Varian, Inc.; Palo Alto, Calif.) at 25° C. in DMSO, at a concentration of 100 nM. The excitation and emission slits were 5 nm, the scan rate was 600 nm/min, and the data interval was 1 nm.

Animal Preparation

C57BL/6 mice and C3Fe.SWV-Mbp$^{shi}$/J shiverer mice were obtained from Jackson Laboratory, Bar Harbor, Minn.

Focal demyelination of adult rat brain. Sprague Dawley female rats (Harlan Laboratory, Indianapolis, Ind.), 12 weeks of age, were used for this study. Animal surgery and care was performed in accordance with the Institutional Animal Care and Use Committee of Case Western Reserve University Animals were anesthetized using a mixture of ketamine hydrochloride (64.2 mg/kg), xylazine hydrochloride (12.9 mg/kg), and acepromazine (12.9 mg/kg) and positioned in a stereotaxic frame (Stoelting). A small incision was made in the scalp, and the corpus callosum was targeted using the following stereotaxic coordinates, relative to bregma: anterior-posterior, 0.0 mm; medial-lateral, 2.0; and dorsal-ventral, 3.4. A small hole was drilled in the skull, and a 26 S gauge needle attached to a 10 µl Hamilton Syringe was lowered into the corpus callosum according to the dorsal-ventral coordinate. A microinjector pump (Stoelting) controlled the infusion of 6 µl of lysolethicin (lysophosphatidyl chorine) or saline at a rate of 0.25 µl/min, after which the needle was left in place for 2 min to prevent liquid reflux out of the brain parenchyma. The incision was then closed using 5-0 Ethicon sutures, and the animals were allowed to recover on a heating pad. The imaging of demyelination of the rats and vehicles were performed 5 d after surgery. The rats were kept alive.

Tissue Processing

Fresh frozen section: Mice or rats were deeply anesthetized with isoflurane and perfused via the ascending aorta with PBS followed by 4% paraformaldehyde in PBS. Brains were removed and incubated for 24 hr in 4% paraformaldehyde at 4° C. Brain tissue was rinsed in PBS, and then incubated in 30% sucrose until submerged. For preparation of fresh-frozen sections, the cryoprotected tissues were first frozen in OCT on dry ice before axial sectioning (20 µm) with a cryostat at −20° C. Tissue from the midline of the brain containing the whole corpus callosum was selected for staining Stained sections were covered with fluorescence mounting medium (Vectashield; Vector Laboratories, Burlingame, Calif.) and stored at 4° C. for future analysis.

Immunohistochemistry

After incubation with 3% normal goat serum in 1×PBS for 60 min, the fresh frozen sections were immunostained overnight at 4° C. with purified SMI99 mouse monoclonal anti-MBP (Covance, Inc. Princeton, N.J.) 1:500 dilution in 3% normal goat serum in 1×PBS, followed by one hour incubation at room temperature with Fluorescein (FITC) AffiniPure Goat Anti-Mouse IgG (H=L) (Jackson ImmunoResearch Laboratories, Inc. West Grove, Pa.) 1:500 dilution, then rinsed in 1×PBS (2×5'). The stained sections were covered with fluorescence mounting medium (Vectashield, Vector laboratories). Images of the stained mouse brain sections were acquired on a Leica DM5000 inverted microscope (L5 filter, BP 527/30).

Black-Gold II Staining

The sections were washed with saline, incubated for 20 min with 0.3% Black-Gold II solution at 60° C., washed twice with saline, the stained sections were covered with fluorescence mounting medium (Vectashield, Vector laboratories). Images of the stained mouse brain sections were acquired on a Leica DMI6000 inverted microscope (Brightfield).

CNP Staining

Fresh frozen sections with 20 μm thickness were incubated in 0.1% Triton-100 in 1×PBS for 10 min, which was followed by incubation in a solution of CNP (1 mM) in 1% DMSO/1×PBS for 30 min at room temperature. The fresh frozen sections were then washed three times for 5 min each with 1×PBS before cover-slipping with fluorescence mounting medium (Vectashield, Vector laboratories). Images of the stained mouse brain sections were acquired on a Leica DMI5000 inverted microscope (Y5 filter, BP 700/75).

Near-Infrared Fluorescence In Vivo Imaging

The in vivo near-infrared fluorescence imaging was carried out using a Xenogen IVIS Imaging System 200, Caliper Life Science. Inc., Hopkinton, Mass. To avoid the influence of autofluorescence and light scattering due to the fur, all the mice or rats were shaved before the experiment. After the i.v. injection of CNP 0.2 mg/kg, the mouse or rat was anesthetized utilizing isoflurane gas, then positioned on the center of the stage (working temperature 20-40° C.) and near-infrared images were acquired by back-thinned, back-illuminated grade 1 CCD, which was thermoelectrically cooled to −90° C. to ensure a low dark current and low noise. The fluorescent filter was set for excitation at 705-780 nm and for emission from 810-885 nm. The experiments were controlled with a Living Image 3.1 (Caliper Life Science. Inc., Hopkinton, Mass.). Lens: f/2. Field of view: 6.5 cm×6.5 cm. Imaging Pixels: 2048×2048. Exposure time: 0.5 s for all of the images.

Radiosynthesis

[$^{11}$C]Carbon dioxide was produced by Scanditronix MC17 and bubbled into a reaction vial filled with LiAlH$_4$ in tetrahydrofurane (THF) solution (0.1 mol/L, 1 ml) at room temperature. After THF was completely evaporated, hydriodic acid (HI, 57%, 1 ml) was added and the reaction vial was heated to 120° C. The [$^{11}$C]methyl iodide obtained then distilled into a vial containing the precursor CNP0 (3 mg) and potassium carbonate (10 mg) in dimethylformamide (0.5 ml). After reacting for 10 minutes at 140° C., the resulting mixture was subjected to a pre-purification procedure using solid-phase extraction on C-18 Sep-Pak cartridge prior to semi-preparative HPLC purification. Briefly, the reaction mixture was diluted with water and loaded onto a C-18 Sep-Pak cartridge. The cartridge was washed with 10 ml of water and dried with a rapid air bolus to remove unreacted [$^{11}$C]CH$_3$I, potassium carbonate, and reaction solvent. The crude product was then slowly eluted with 1 ml of ethanol and subjected to an HPLC purification process using a Phenomenex C-18 column (250 mm×10 mm, 0.1% TFA/acetonitrile: 0.1% TFA/H2O=75:25, flow rate 3.0 ml/min) The radioactive fraction containing [$^{11}$C] CNP was collected, after evaporation, the residue was re-dissolved in 5% DMSO in saline solution, and filtered (0.22 μm) into a sterile injection bottle for animal use. In the meantime, [$^{11}$C] CNP was either allowed to stand at room temperature for 4 hrs or diluted with saline. The radiochemical purity of both the original and diluted aqueous solutions was assayed by HPLC for in vitro stability assay.

MicroPET-CT Studies

Animals were placed in a Concord R4 microPET scanner (Knoxville, Tenn.) under anesthesia. After a 10 min transmission scan with a Co-57 source, 7.4 MBq of [11C]DAS were administered to each animal through a tail vein injection, which was immediately followed by dynamic acquisition for up to 90 min. A 2-D filtered back projection (FBP) algorithm was used for image reconstruction with a 256×256 pixel resolution per transverse slice. A total of 63 transverse slices were reconstructed with the field of view covering the head of the animals. Decay correction, attenuation correction and scatter correction were all performed during the image histogram and reconstruction processes.

Magnetic Resonance Imaging (MRI) Studies

All MR imaging experiments were performed on a Bruker Biospec 7.0T/30 cm MRI and Spectroscopy scanner (Bruker Biospin, Billerica, Mass.). The animal's head was positioned in a 72-mm volume ID cylindrical transceiver coil. A RARE acquisition (TR/TE=2000/40 ms, 4 echoes, FOV=45 mm×45 mm, matrix=256×256) was used to acquire 15 contiguous 1-mm axial images of each animal's brain.

Co-Registration of Images and Statistical Analysis

The near-infrared images were evaluated with a Living Image 3.1 from Caliper Life Science. Inc., Hopkinton, Mass. All the images used photon as the unit for the quantification, and the images were shown as an overlaid photograph with fluorescence. Statistical analysis was performed using a two-tailed t-test with GraphPad Prism 5, La Jolla, Calif.

Coregistration of MRI and PET images, PET and CT images were conducted by using the MATLAB-based program COMKAT (Compartmental Model Kinetic Analysis Tool). The registration was conducted using a coronal view of the mice. After creating uniform images from the PET and MRI images, VOI (Volume of interest) and ROI (Region of interest) were defined and used to measure the radioactivity concentration in the corpus callosums of both hypomyelinated and wild type mice. Multiple time activity curves were then obtained for statistical analysis.

The radioactivity was decay-corrected and normalized by the body weight of the mice and the amount of [$^{11}$C] CNP injected. The resulting normalized time-activity curves obtained from different data sets were averaged to provide normalized time-activity curves for the experiments. A student t-test was used to evaluate if there was any significant difference between the curves with a p value <0.05.

Results

Fluorescent Properties of CNP

CNP is a highly conjugated dibenzothiazol derivative with a structure shown in FIG. 9A. The fluorescent excitation and emission spectra of CNP were recorded using Varian fluorescent spectroscopy at a concentration of 100 nM in DMSO. As shown in FIG. 9B, the excitation and emission maxima of CNP are 786 nm and 804 nm, respectively, which are located in the near infrared region (650 nm-900 nm).

In Vitro Binding Studies

The myelin-binding property of CNP was first examined by fluorescent tissue staining of wild-type mouse and shiverer mouse brain sections. For comparison, immunohistochemical staining with myelin-specific MBP antibody was also conducted. At 1 mM concentration, CNP selectively labeled intact myelin sheaths present in the whole mouse brain, particularly in the corpus callosum (FIG. 9E, F). The pattern of myelin sheaths stained by CNP was virtually identical to the pattern stained by MBP antibody (FIG. 9C, D). These observations indicated that CNP binds specifically to myelin sheaths in vitro.

To determine the exact binding sites of CNP, we compared both CNP and MBP staining conducted in the same brain tissue sections. Each section was first subjected to CNP staining (FIG. 9G, J, M), followed by antibody staining of MBP (FIG. 9H, K, N). The antibody staining was significantly blocked by CNP in different regions including cerebellum (FIG. 9I), frontal cortex (FIG. 9L) and caudate putaman (FIG. 9O). The results indicate that CNP binds specifically to MBP present in the CNS myelin.

In Vivo NIRF Imaging of Myelin in Shiverer Mouse Model

We then evaluated the pharmacokinetic profiles of CNP in 3-month old female shiverer mice (n=3) and age-matched wild-type mice (n=3). In vivo NIR imaging was conducted using the same dosage (0.1 mg/kg). The fluorescent signals were recorded at pre-injection, 5, 10, 15, 20, 25, 30, 40, 50, 60, 70, 80 and 90 min after i.v. injection of CNP and the vehicle (0.05% DMSO/PBS (V/V)). As shown in FIGS. 10A and 10B, the fluorescent intensities in the brain between the shiverer mice and wild-type models were significantly different.

Based on these images, quantitative analyses were conducted to determine the time course of fluorescent radiance. As shown in FIG. 11C, the average radiance at 30 minutes in wild-type mice is four fold greater than that observed in shiverer mice. Since shiverer mice are deficient in CNS myelin, the fluorescent signal originating from shiverer mice is very weak, even at its peak at 5 min. These results further demonstrated that accumulation of CNP in the brain is proportional to the myelin content and can be used as a surrogate marker of myelination.

In Vivo microPET-MR-NIRF Imaging of Myelin in Focal Demyelination Rat Model

In this study, we used a rat model of focal CNS demyelination for microPET-MR-NIRF imaging studies to take advantage of the relatively large size of the brain. The demyelinating agent lysolethicin was delivered to one hemisphere of the corpus callosum and the saline was delivered into the rat brains as vehicles. We conducted the microPET-MR imaging first. The axial views of both vehicle and lysolethicin-treated rat brains are used to highlight the corpus callosum region. As shown in FIG. 12, the anatomy of the rat brain and the focal lesion of demyelination induced in the corpus callosum region are illustrated by MRI images, which have been coregistered with microPET images. In comparison with the normal control rat, focal demyelination is readily detected 5 d after stereotaxic injection of lysolethicin to one hemisphere of corpus callosum, where the retention of [11C] CNP is significantly decreased as indicated by the fused PET images. [11C] CNP preferentially localizes in the myelin-rich white matter versus the myelin deficient gray matter. For quantitative analysis, the microPET images were then registered with MR images for quantification of radioactivity concentrations. The left hemisphere of the corpus callosum, where demyelination was induced, was selected as the ROI for comparison. The average radioactivity concentrations during 0-60 min were determined. As shown in FIG. 12, the uptake of [11C] CNP in control rat brain was significantly higher than that in demyelinated rat brain, and as expected, the uptake of [11C] CNP in demyelinated rat brain was significantly lower than that in remyelinated rat brain throughout the 60 min of microPET scan. In the corpus callosum, the average standardized uptake value (SUV) in the demyelinated region was 40 and 20% lower than those in the control myelinated region and remyelinated regions, respectively.

After NIRF imaging, we compared the ability of the CNP to detect the myelin loss in CNS, a characteristic of the lysolethicin model of rat demyelination. Black-Gold II staining on adjacent sections of the corpus callosum was used for comparison. These results suggest that the CNP-PET-NIRF is a valid imaging marker for visualizing and quantifying myelin sheaths under both normal and pathophysiological conditions.

The present invention is not to be limited in scope by the specific embodiments described herein. Indeed, various modifications of the invention in addition to those described herein will become apparent to those skilled in the art from the foregoing description and accompanying Figures. Such modifications are intended to fall within the scope of the appended claims. Various references are cited herein, the disclosure of which are incorporated by reference in their entireties.

Having described the invention, the following is claimed:

1. A method of detecting myelin in vivo in a subject's tissue, the method comprising:
   (i) administering to the subject a molecular probe including a compound having the general formula selected from the group consisting of:

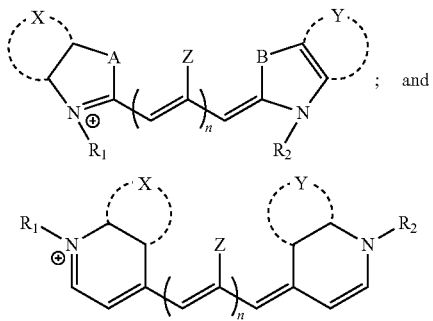

wherein n is an integer from 1 to 10; A, B each independently represent $CR'_2$, O, S, NH, $CH_2CH_2$, CH=CH; $R_1$, $R_2$, R', and Z each independently represent H, alkyl, alkenyl, alkynyl and/or an aryl group; X and Y each independently represent

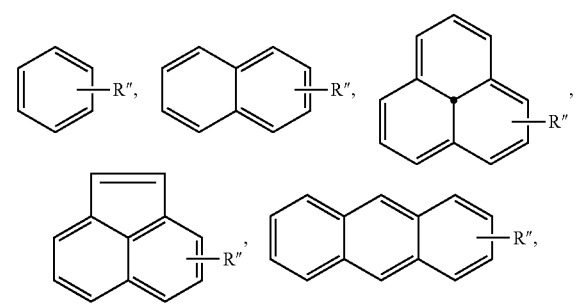

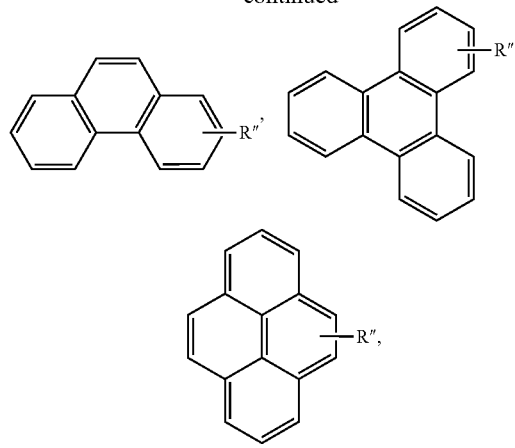, or

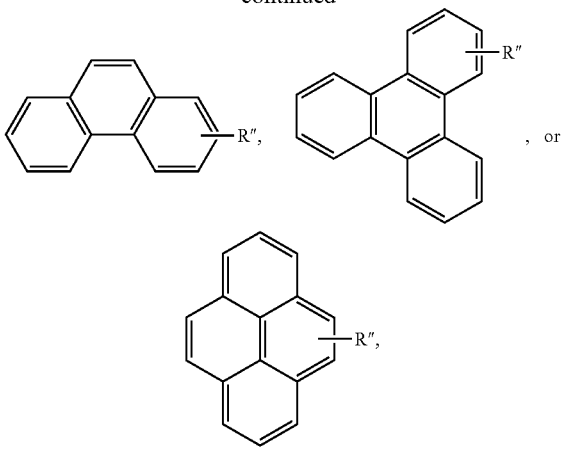, or wherein R"=H, alkyl, alkenyl, alkynyl or an aryl group; and pharmaceutically acceptable salts thereof; and (ii) detecting the location, distribution, and/or amount of the compound that is bound to the myelin to detect the myelin in the tissue.

2. The method of claim 1, wherein $R_1=R_2$.
3. The method of claim 1, wherein A=B.
4. The method of claim 1, wherein X=Y.
5. The method of claim 1, the molecular probe further comprising a radiolabel.
6. The method of claim 1, the molecular probe further comprising a magnetic resonance contrast agent that is bound to the molecular probe to facilitate or enhance magnetic resonance imaging of the molecular probe.
7. The method of claim 1, the molecular probe including a compound having the general formula:

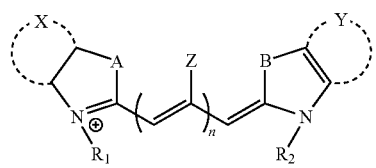

wherein n is an integer from 1 to 10; A, B each independently represent $CR'_2$, O, S, NH, $CH_2CH_2$, CH=CH; $R_1$, $R_2$, R', and Z each independently represent H, alkyl, alkenyl, alkynyl and/or an aryl group; X and Y each independently represent

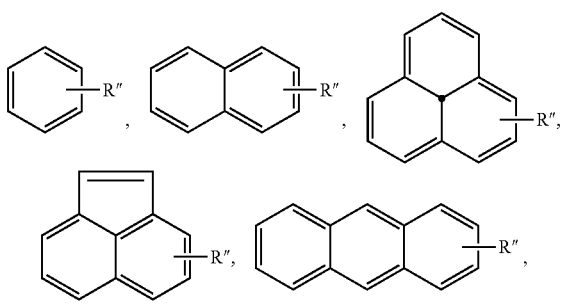

wherein R"=H, alkyl, alkenyl, alkynyl or an aryl group; and pharmaceutically acceptable salts thereof.

8. The method of claim 7 comprising the formula:

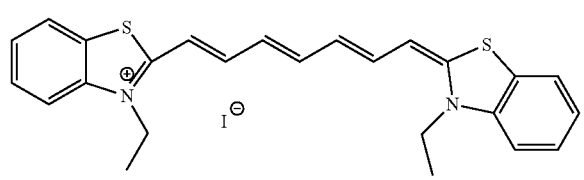 [SMILES: CCN1\C(=C/C=C/C=C/C=C/c2sc3ccccc3[n+]2CC)Sc2ccccc21 ; [I-]]

and pharmaceutically acceptable salts thereof.

9. The method of claim 7, the molecular probe including a compound having the formula:

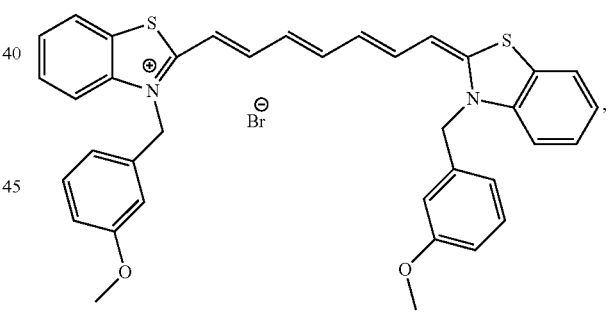

and pharmaceutically acceptable salts thereof.

10. The method of claim 1, the molecular probe including a compound having the general formula:

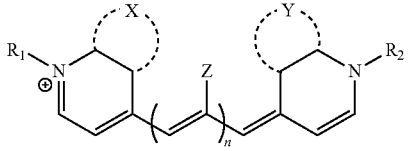

wherein n is an integer from 1 to 10; $R_1$, $R_2$, R', and Z each independently represent H, alkyl, alkenyl, alkynyl and/or an aryl group; X and Y each independently represent

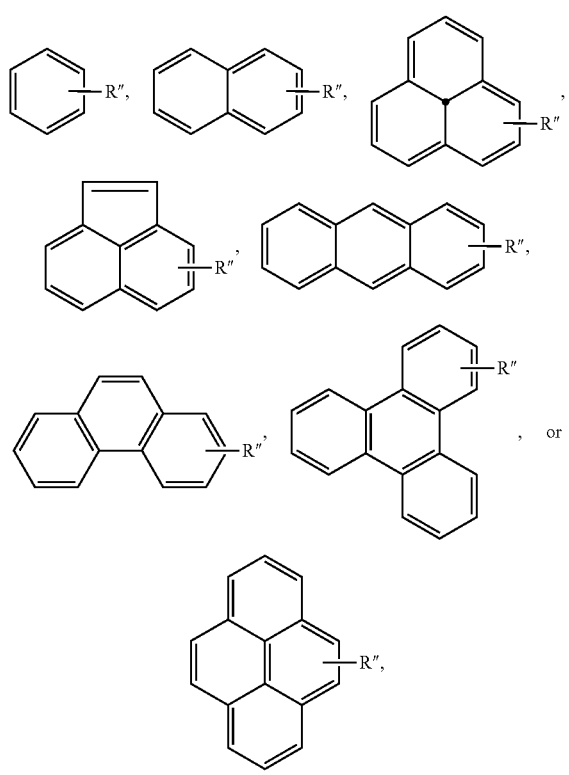

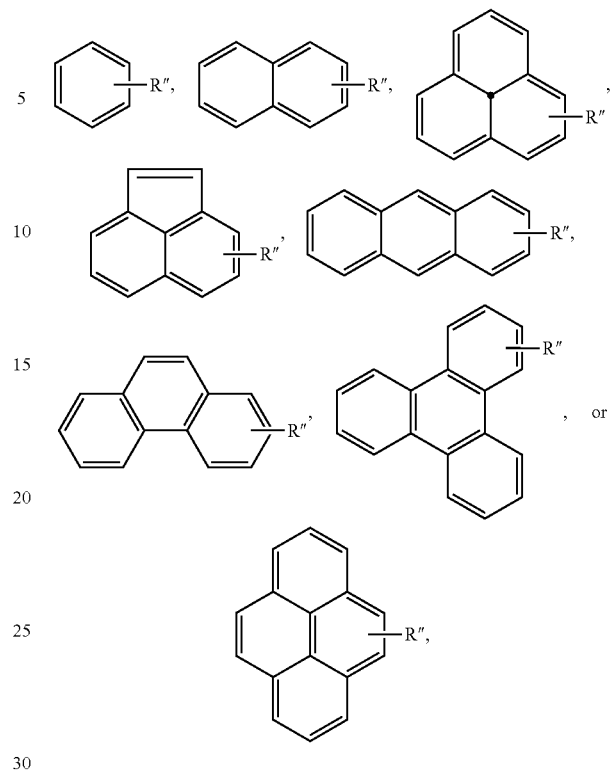

wherein R"=H, alkyl, alkenyl, alkynyl or an aryl group; and pharmaceutically acceptable salts thereof.

11. The method of claim 1, wherein the location, distribution, and/or amount of the compound is detected using in vivo imaging modality comprising a near-infrared fluorescence imaging modality.

12. The method of claim 1, the in vivo imaging modality comprising a fluorescence molecular tomography imaging modality.

13. The method of claim 1, further comprising the step of administering the molecular probe to the subject parenterally.

14. A method of detecting myelin in vivo in a subject's tissue, the method comprising:

(i) administering to the subject a molecular probe including a compound having the general formula of:

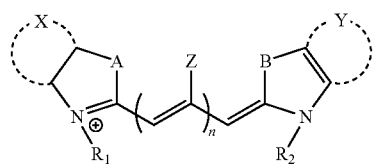

wherein n is an integer from 3 to 10; A, B each independently represent $CR'_2$, O, S, NH, $CH_2CH_2$, CH=CH; $R_1$, $R_2$, R', and Z each independently represent H, alkyl, alkenyl, alkynyl and/or an aryl group; X and Y each independently represent wherein R"=H, alkyl, alkenyl, alkynyl or an aryl group; and pharmaceutically acceptable salts thereof; and (ii) detecting the location, distribution, and/or amount of the compound that is bound to the myelin to detect the myelin in the tissue.

15. The method of claim 14, wherein $R_1$=$R_2$.
16. The method of claim 14, wherein A=B.
17. The method of claim 14, wherein X=Y.
18. The method of claim 14, the molecular probe further comprising a radiolabel.
19. The method of claim 14, the molecular probe further comprising a magnetic resonance contrast agent that is bound to the molecular probe to facilitate or enhance magnetic resonance imaging of the molecular probe.
20. The method of claim 14, the molecular probe including a compound having the formula:

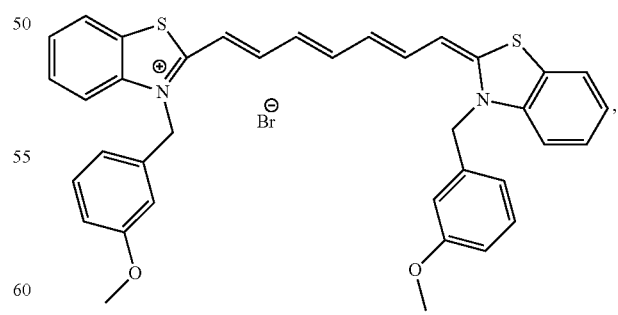

and pharmaceutically acceptable salts thereof.

21. The method of claim 14, wherein the location, distribution, and/or amount of the compound is detected using an in vivo imaging modality comprising a near-infrared fluorescence imaging modality.

22. The method of claim 14, further comprising the step of administering the molecular probe to the subject parenterally.

\* \* \* \* \*